US005760027A

United States Patent [19]

Buynak et al.

[11] Patent Number: 5,760,027
[45] Date of Patent: Jun. 2, 1998

[54] USE OF 7-ALKYLIDENE CEPHALOSPORINS TO INHIBIT ELASTASE ACTIVITY

[75] Inventors: John D. Buynak; Akireddy Srinivasa Rao; Greg C. Adam, all of Dallas, Tex.

[73] Assignee: Research Corporation Technologies, Inc., Tucson, Ariz.

[21] Appl. No.: 767,103

[22] Filed: Dec. 6, 1996

[51] Int. Cl.$^6$ .................... C07D 501/20; A61K 31/545
[52] U.S. Cl. .................... 514/200; 540/215; 540/223; 540/228; 540/230; 514/202; 514/209
[58] Field of Search .................... 540/215, 223; 514/200, 202, 209

[56] References Cited

U.S. PATENT DOCUMENTS

| | | | |
|---|---|---|---|
| 4,150,156 | 4/1979 | Beattie et al. | 424/246 |
| 4,547,371 | 10/1985 | Doherty et al. | 514/200 |
| 4,637,999 | 1/1987 | Doherty et al. | 514/201 |
| 4,992,541 | 2/1991 | Blacklock et al. | 540/221 |
| 5,077,286 | 12/1991 | Bissolino et al. | 514/201 |
| 5,126,446 | 6/1992 | Brown, Jr. et al. | 540/230 |
| 5,258,377 | 11/1993 | Marti et al. | 540/221 |
| 5,264,429 | 11/1993 | Maiti et al. | 514/202 |
| 5,348,952 | 9/1994 | Bissolino et al. | 514/202 |
| 5,356,888 | 10/1994 | Alpegiani et al. | 514/204 |
| 5,364,848 | 11/1994 | Doherty et al. | 514/201 |
| 5,446,037 | 8/1995 | Maiti et al. | 514/201 |

OTHER PUBLICATIONS

Applegate, H.E., et al., "7-[2-Hydroxyethyl]Cephalosporanic Acid Derivatives", *Tetrahedron Letters*, No. 19, pp. 1637-1640, (1979).

Buynak, J.D., et al., "Synthesis and biological activity of 7-alkylidenecephems", *J. Med. Chem.*, 38, 1022-1034, (1995).

Buynak, J.D., et al., "Synthesis and mechanistic evaluation of 7-vinylidenecephem sulfones as B-lactamase inhibitors", *J. of Am. Chem. Soc.*, 116, 10955-10965, (1994).

Chandrasekaran, S., et al., "Synthesis of Substituted B-Lactams by Addition of Nitromethane to 6-Oxepenicillanates and 7-Oxocephalosporanates", *J. Org. Chem.*, vol. 42, No. 24, pp. 3972-3974, (1977).

Doherty, J.B., et al., "Inhibition of human leukeocyte elastase. 1. Inhibition by C-7-substituted cephalosporin tert-Butyl esters", *J. Med. Chem.*, 33, 2513-2521, (1990).

Finke, P.E., et al., "Inhibition of human leukocyte Elastase. 4. Selection of a substituted cephalosporin (L-658,758) as a topical aerosol", *J. Med. Chem.*, 35, 3731-3744, (1992).

Knight, W.B., et al., "Specificity, stability, and potency of monocyclic B-Lactam inhibitors of human leucocyte elastase", *Biochemistry*, 31, 8160-8170, (1992).

Navia, M.A., et al., "Crystallographic study of a B-lactam inhibitor complex with elastase at 1.84 A resolution", *Nature*, 327, 79-82, (1987).

Shah, S.K., et al., "Inhibition of human leukocyte Elastase. 3. Synthesis and activity of 3'-substituted cephalosporins", *J. Med. Chem.*, 33, 2529-2535, (1990).

Uyeo, S., et al., "Snythesis of (6R, 7R)-Phenylacetylmethyl- 3(1-Methyl-1H-Tetrazol-5-yl) Thiomethyl-1-)xa-1-Dethiace phalosporanic Acid", *Heterocycles*, vol. 13, pp. 255-257, (1979).

*Primary Examiner*—Mukund J. Shah
*Assistant Examiner*—King Lit Wong
*Attorney, Agent, or Firm*—Schwegman, Lundberg, Woessner & Kluth, P.A.

[57] ABSTRACT

The present invention relates to the use of 7-alkylidene derivatives of cephalosporin esters, such as sulfides, sulfoxides, and sulfones, as inhibitors of human leukocyte elastase. These materials are therefore useful as anti-inflammatory and anti-degenerative agents.

41 Claims, 1 Drawing Sheet

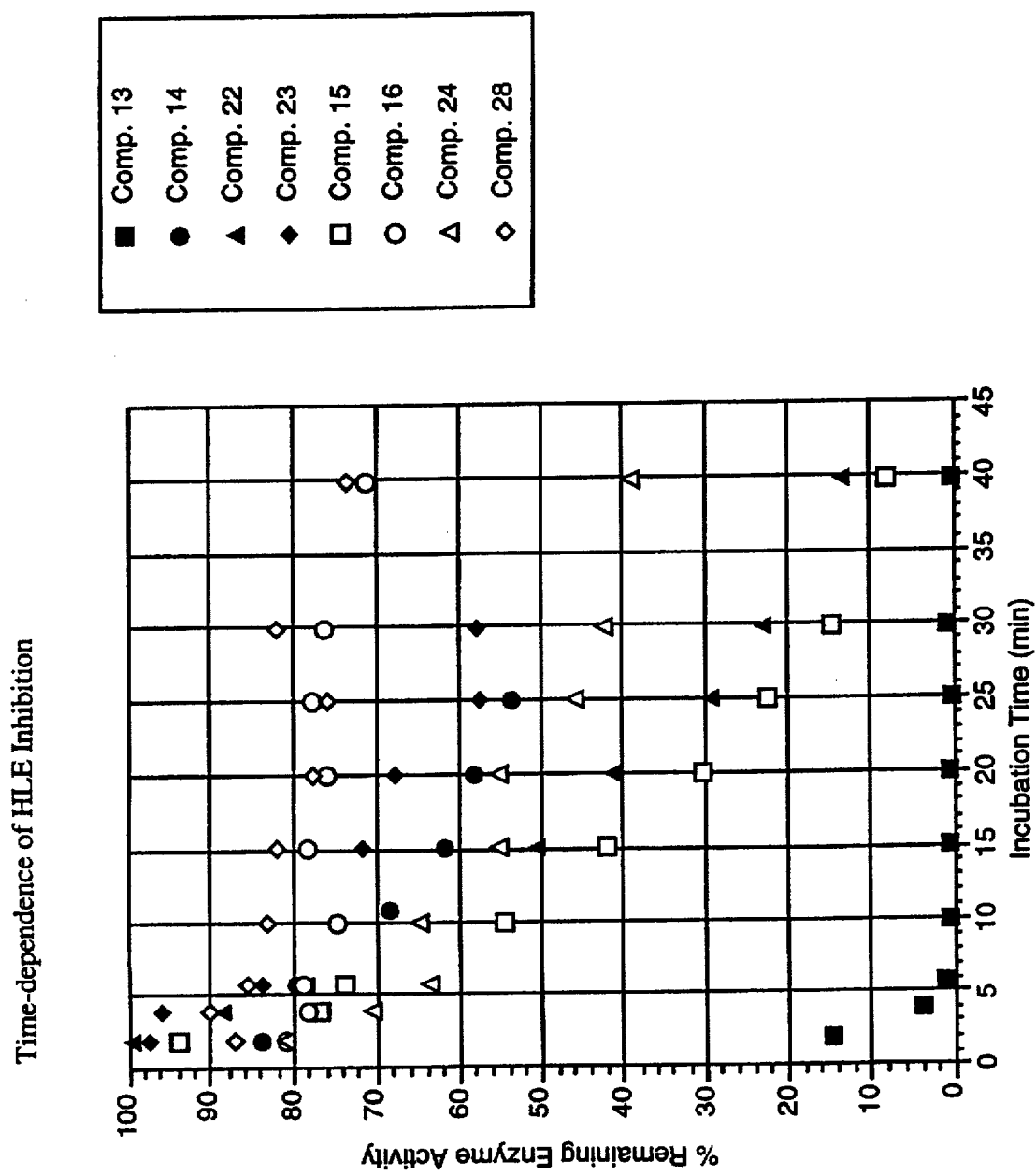

USE OF 7-ALKYLIDENE CEPHALOSPORINS TO INHIBIT ELASTASE ACTIVITY

BACKGROUND OF THE INVENTION

This application was made with the support of NIH Grant RO1-GM37774. The U.S. Government has certain rights in this invention.

Human leukocyte elastase (HLE) is a potent serine proteinase which has been implicated in the chronic tissue destruction mechanisms of several disease states including emphysema, acute respiratory distress syndrome (ARDS), atherosclerosis, and rheumatoid arthritis. HLE is stored in the azurophilic granules of polymorphonuclear leukocytes (PMN's) and is released in response to inflammatory stimuli. Under normal circumstances, it is believed that an appropriate balance exists between released HLE and endogenous inhibitors, which scavenge the enzyme. However, in certain disease states an imbalance occurs. This is usually due to the liberation of excessive HLE or to the impairment of the regulatory processes. Since HLE is capable of degrading a variety of structural proteins, including elastin, other components of connective tissue, certain complement proteins and receptors, widespread tissue destruction ensues. In cigarette smokers, this imbalance can occur because of the oxidative inactivation of α-1-proteinase, an endogenous HLE inhibitor, by the smoke. Free HLE has been detected in the lung fluid of patients with chronic bronchitis and cystic fibrosis.

A proposed treatment of such diseases involves the administration of HLE inhibitors. For example, S. Maiti et al. (U.S. Pat. No. 5,446,037) and J. B. Doherty et al. (U.S. Pat. No. 5,364,898) disclose that certain cephalosporin sulfones are active as elastase inhibitors, and can be useful as anti-inflammatory and anti-degenerative agents.

However, a continuing need exists for potent inhibitors of mammalian elastases which will be useful in the control of tissue damage and various inflammatory or degenerative conditions mediated by elastase and like proteinases.

SUMMARY OF THE INVENTION

The present invention provides a method of treating elastase-mediated pathologies comprising the administration to a mammal in need of such treatment an effective amount of a compound of formula I:

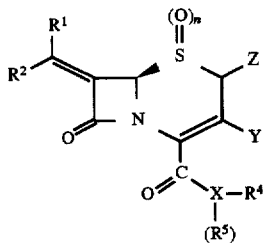

wherein n=0, 1, or 2;

$R^1$ and $R^2$ are the same or different and are:
a) hydrogen;
b) halo (F, Cl, Br, I);
c) $(C_1-C_{10})$alkoxycarbonyl; preferably $(C_1-C_4)$ alkoxycarbonyl;
d) cyano (CN);
e) $(C_1-C_{10})$alkoxycarbamido; preferably $(C_1-C_4)$ alkoxycarbamido;
f) a 5-7 membered heterocyclic ring;
g) $(C_1-C_{10})$alkyl;
h) $(C_2-C_{10})$acyl; preferably acetyl;
i) $(C_1-C_{10})$alkoxy; preferably methoxy;
j) $N(R)_2$, wherein each R is H, $(C_1-C_{10})$alkyl, phenyl or benzyl; preferably $N(R)_2$ is amino;
k) $(R)_2NC(O)$—; preferably formamido;
l) $NO_2$;
m) N=O;
n) S(R);
o) $(C_6-C_{10})$aryl; or
p) $CO_2H$;

Z is:
a) halo;
b) CHO;
c) $CO_2H$;
d) CN;
e) $(C_1-C_{10})$alkyl;
f) $(C_6-C_{10})$aryl;
g) $C(O)R^7$;
h) $CO_2R^7$;
i) $OR^7$;
j) $OC(O)R^7$;
k) $SR^7$;
l) $SC(O)R^7$;
m) $N(R^7)_2$; or
n) H;

Y is:
a) —$CH_2A$ wherein A is:
(i) H;
(ii) halo;
(iii) OH;
(iv) $(C_1-C_{10})$alkoxy; preferably $(C_1-C_4)$alkoxy;
(v) $(C_6-C_{10})$aryloxy;
(vi) $(C_2-C_{10})$alkanoyloxy; preferably acetoxy;
(vii) $N(R)C(O)R^7$;
(viii) —$N(R)_2$;
(ix) S(R);
(x) $SC(O)(C_1-C_{10})$alkyl;
b) halo, preferably Cl or F;
c) CHO;
d) $CO_2H$;
e) CN;
f) $(C_1-C_{10})$alkyl;
g) $(C_6-C_{10})$aryl;
h) $C(O)R^7$;
i) $CO_2R^7$;
j) $OR^7$;
k) $OC(O)R^7$;
l) $SR^7$;
m) $SC(O)R^7$;
n) $N(R^7)_2$; wherein each $R^7$ is $(C_1-C_{10})$alkyl, $(C_6-C_{10})$ aryl, or a 5-10 membered heterocyclic ring;

X is $CR^8$, O, S or N; preferably $CR^8$; wherein $R^4$ and $R^5$, if present, are the same or different and are:
a) $(C_1-C_{10})$alkyl;
b) $(C_6-C_{10})$aryl; preferably phenyl;
c) a 5-10 membered heterocyclic ring; or
d) H; with the proviso that if X is O, $R^4$ is not H; wherein $R^8$ is H or $R^4$; wherein alkyl or alkoxy are optionally substituted with 1-3 $(C_1-C_{10})$alkyl, preferably $(C_1-C_4)$alkyl, OH, halo, phenyl or mixtures thereof; wherein aryl or aryloxy are optionally substituted with 1-3 $(C_1-C_4)$alkyl, OH, $(C_1-C_4)$alkoxy, halo, phenyl or mixtures thereof; wherein the heterocyclic ring comprises 1-3 N(R), S or nonperoxide O, wherein R is absent or is H, $(C_1-C_4)$alkyl, phenyl or benzyl; or a pharmaceutically acceptable salt thereof.

Novel compounds within the scope of formula I are also within the scope of the invention, and are useful as elastase inhibitors, as beta-lactamase inhibitors or as intermediates for the preparation thereof. Also within the scope of the invention are pharmaceutical compositions and unit dosage forms comprising an effective elastase-inhibitory amount of one or more of the compounds of formula I in combination with a pharmaceutically acceptable vehicle.

DETAILED DESCRIPTION OF THE INVENTION

As used herein, the term alkyl includes branched or straight chain alkyl, optionally comprising 1-3 double bonds, preferably one double bond, and includes cycloalkyl, (cycloalkyl)alkyl and alkyl(cycloalky)alkyl. Preferably, alkyl is $(C_1-C_4)$alkyl.

Heterocyclic rings useful as substituents in formula I include 5-7 membered heterocyclic rings, including heteroaryl moieties such as pyridinyl, triazolyl, triazinyl, oxazoyl, isoxazolyl, oxazolidinoyl, isoxazolidinoyl, thiazolyl, isothiazolyl, pyrazolyl, imidazolyl, pyrrolyl, pyrazinyl, morpholinyl, quinolinyl, isoquinolinyl, indolyl, thiophenyl, and pyrimidinyl.

A is preferably $(C_2-C_{10})$alkanoyloxy, most preferably $(C_1-C_4)$alkanoyloxy; i.e., OAc. X is preferably C, Z is preferably H, and one of $R^1$ and $R^2$ is preferably other than H.

Pharmaceutically acceptable salts include the non-toxic acid addition salts of nitrogen-containing substituents such as amino groups, N-containing heterocycles and substituted amines, i.e., the quaternary ammonium salts ($NH_4^+$, $N(R^7)_3$ $H^+$, $N(R^7)_4^+$) and the metal ion or ammonium ion salts of carboxylic acids.

Pharmaceutically acceptable amine salts may be salts of organic acids, such as acetic, tartaric, citric, lactic, malic, maleic, tartaric, p-toluene sulfonic acid, methane sulfonic acid, and the like as well as salts of pharmaceutically acceptable mineral acids such as phosphoric, hydrochloric or sulfuric acid, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide; or with an amine.

As shown in Table 1, compounds of three general structural types, A, B, and C were synthesized and evaluated for the ability to inhibit HLE. Compounds of type C have been previously reported (Doherty et. al., *J. Med. Chem.*, 33, 2513 (1990)) and were prepared here for comparison purposes only. Compounds of type B had been previously prepared (Buynak et. al., *J. Am. Chem. Soc.*, 116, 10955 (1994)) but were evaluated as HLE inhibitors here for the first time. Compounds of type A, which are specific examples of the general structure formula I, are the subject of this present patent application.

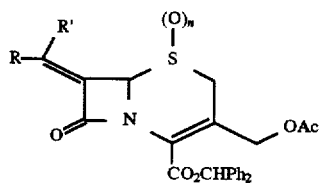

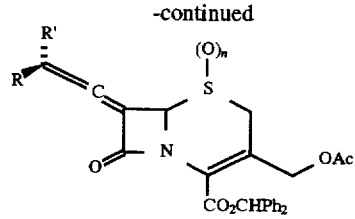

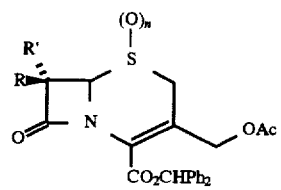

Compounds of formula I are obtained as shown in Scheme 1 (below). 7-Aminocephalosporanic acid (commercially available) was esterified by treatment with diphenyldiazomethane to produce the corresponding benzhydryl ester (1). 1 was then oxidized to the corresponding ketone, 2, by treatement with triflic anhydride in the presence of triethylamine, followed by acidic hydrolysis of the resultant sulfonylimine according to the proceedure of Hagiwara (D. F. Hagiware et. al., *J. Chem. Soc. Chem. Commun.*, 578 (1982)). This ketone was then used without further purification.

The 7-alkylidenecephalosporanates of general formula I were then prepared by treating 2 with the corresponding Wittig reagent at −78° C. All of the sulfides (n=0) were prepared in this manner with the exception of compound 15, which was prepared by selective reduction of 13 with Zn/Cu couple and compound 26, which was prepared by reduction of 19 with $NaCNBH_3$ as shown below. The corresponding sulfones (n=2) were prepared by treatment with excess m-chloroperoxybenzoic acid as shown.

Scheme 1.
General Synthesis of the 7-Alklidenecephalosporins
(A, n = 0) and Corresponding Sulfones (A, n = 2)

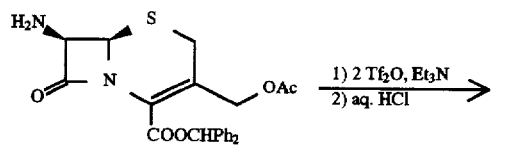

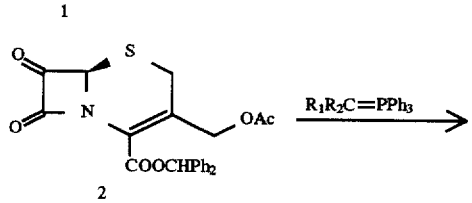

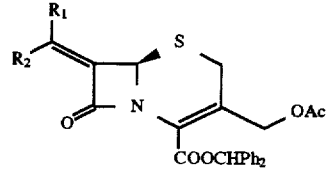

A (n = 0)
(comp. 9, 11, 13, 17, 19, 20, 22, 24, 28, 30, 32)

-continued
Scheme 1.
General Synthesis of the 7-Alklidenecephalosporins (A, n = 0) and Corresponding Sulfones (A, n = 2)

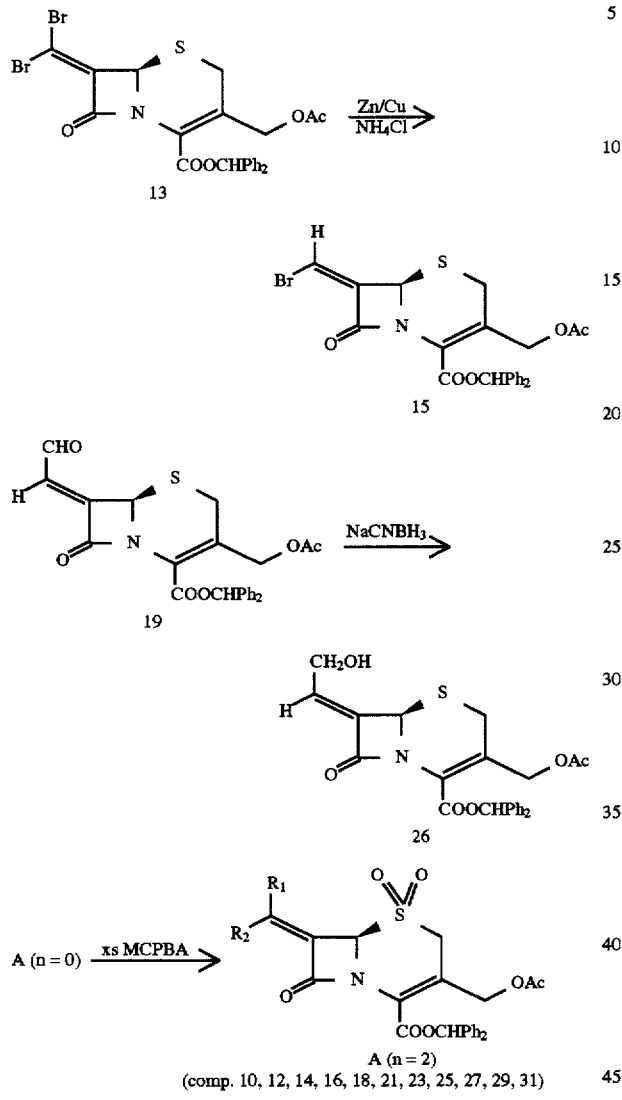

The preparation of the 7-vinylidenecephalosporins is shown below in Scheme 2. These reactions have been previously reported (Buynak et. al., *J. Am. Chem. Soc.*, 116,10955 (1994)).

Scheme 2.
General Synthesis of the 7-Vinylidenecephalosporins (B, n = 0) and Corresponding Sulfones (B, n = 2).

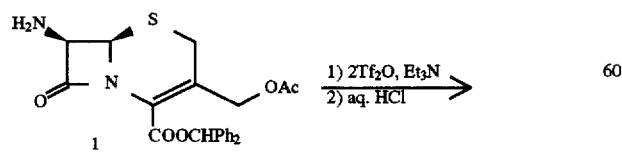

-continued
Scheme 2.
General Synthesis of the 7-Vinylidenecephalosporins (B, n = 0) and Corresponding Sulfones (B, n = 2).

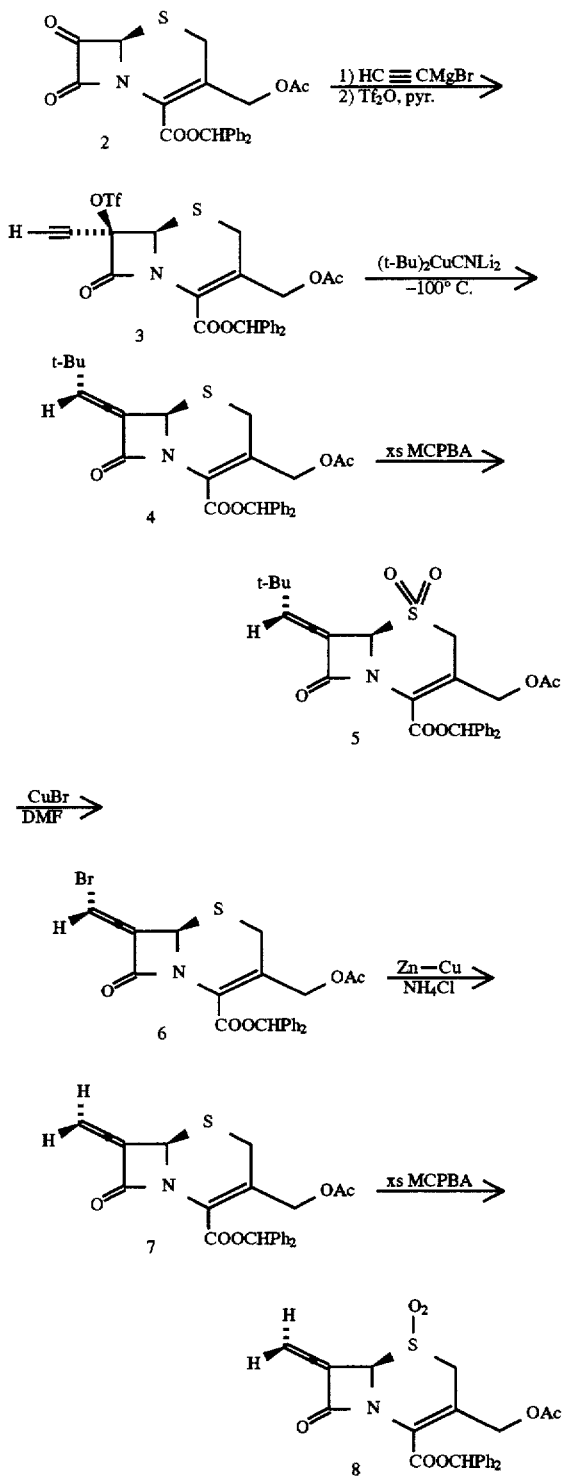

Scheme 3.
General Synthesis of 7-Monosubstituted and Unsubstituted Cephalosporins (C)

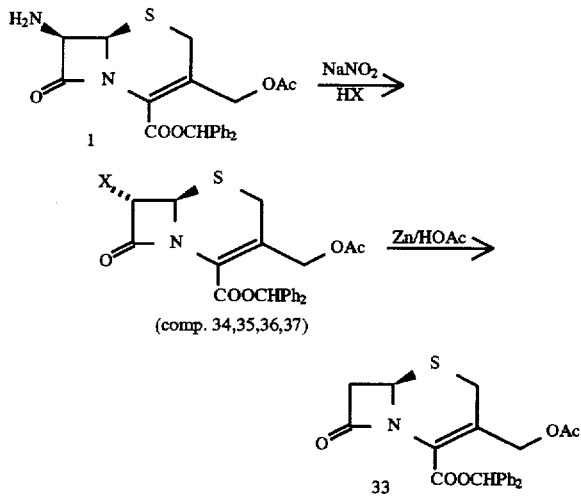

Compounds of formula I containing $R_1$ and $R_2$ groups (i.e., alkoxy or alkene) not shown above may be synthesized by using an appropriate Wittig reagent $R_1R_2C=PPh_3$. The Wittig reagents $ROCH=PPh_3$ and $H_2C=CH-CH=PPh_3$ may be used to make the 7-alkyoxymethylene and 7-alkenylmethylene compounds, respectively.

The compounds wherein A is alkoxy, aryloxy, or arylalkoxy may be obtained by reaction of the 3-hydroxymethyl species with tosyl chloride and displacement of the resultant tosylate with an $R^7O^-$ species. For example, sodium methoxide may be used to obtain the 3-methoxymethyl species. The compounds wherein A is mercapto may be formed by reaction of the 3-chloromethyl compound with sodium sulfydride (NaSH). This compound may further be derivatized with an alkylhalide to form a substituted mercapto or an acylchloride to form an acylthio group.

The species wherein A is an amino group may be formed by the Gabriel Synthesis, i.e., reaction of the 3-chloromethyl compound with potassium phthalimide and hydrolysis of the product with acid to yield the 3-aminomethyl compound. The 3-aminomethyl compound may be formed by reaction of the 3-aminomethyl compound with methyl chloride to form the 3-trimethylammoniomethyl chloride.

The compound wherein A is an amido group ($CONH_2$) may be formed by displacement of the tosylate described above with cyanide, e.g., KCN, followed by hydrolysis of the resulting nitrile to the amide.

In addition to the Wittig reaction, the Peterson olefination procedure may be used to form 7-substituted methylene compounds from the oxocephalosporanate 43. For example, (RO) $(SiMe_3)$ CHLi or (haloalkyl) $(SiMe_3)$ CHLi may add to 43 to form the 7-alkoxymethylene or 7-halomethylmethylene compounds, respectively.

The 7-alkanoylmethylene species may be made by forming the vinyl anion and reacting it with a desirable alkanoyl halide. The vinyl anion may be made by a standard lithium-halogen (or magnesium-halogen) exchange reaction, for example, reaction of 13 with methyl lithium. The lithium vinyl group may then be functionalized by reaction with an alkoxycarbonyl chloride.

The 7-carboxylmethylene compounds ($R_1$ or $R_2$=COOH or COOY) may be formed by hydrolysis of the corresponding ester, preferably, the corresponding t-butyl ester.

The compounds wherein Y is a halogen may be formed by displacement of the —OAc group with ethylxanthate ($EtOCS_2K$). Raney-Nickel desulfurization ($H_2/Ra$—Ni) would yield the exocyclic alkene which may then be ozonized to the 3-hydroxy compound. Reaction with a halogenating reagent would provide the 3-halo species. For example, $PCl_5$ may be used to convert the 3-OH group into a 3-Cl group. The 3-methyl species may be obtained by the rearrangement of the exocyclic alkene, formed by Raney-Nickel desulfurization, by reaction with $Et_3N$. The 3-hydroxymethyl species may be obtained by hydrolysis of the —OAc group with NaOH or an appropriate enzyme. The 3-halomethyl species may be formed by reaction of the 3-hydroxymethyl species with a halogenating reagent. For example, $PCl_5$ may be used to form the 3-chloromethyl species.

The sodium carboxylate salts of 44 and 50 can be prepared by removal of the benzhydryl group with anisole/ $AlCl_3$ in $CH_2Cl_2$, followed by addition of a gaseous $NaHCO_3$, and extraction with ethyl acetate, as disclosed in U.S. patent application Ser. No. 08/354,850, filed Dec. 9, 1994.

The cephalosporin esters of structural formula I where $X(R^4)(R^5)$ is other than hydroxy can be prepared from the corresponding acid according to conventional methods of esterification. For example, a compound of formula I is treated with a lower alkanol, a substituted or unsubstituted benzyl alcohol, or a substituted or unsubstituted benzhydrol (diphenylmethanol) in the presence of a catalyst such as sulfuric acid, hydrochloric acid, an arylsulfonic acid, $BF_3$, DCCD, an acidic ion exchange resin and the like, at from about 0° to about 150° C., with or without refluxing until the esterification is substantially complete. Optionally, an organic solvent may be used to facilitate the reaction. Also, a compound of formula I can be esterified by converting it to an acid halide such as acid chloride or bromide via treatment with a halogenating agent such as thionyl chloride, phosphorus penta- or oxychloride followed by reaction with an appropriate alcohol. Esters of compounds of formula I can also be prepared by alkylation of carboxylate salts (e.g., $K^+$, $Na^+$, $Ca^{++}$, $Ag^+$, $Cu^+$, $-N(R)_4^+$, and $Hg^{++}$ salts) of formula I with alkyl halides, by for example, benzylchloride, benzhydryl chloride; by reaction with alkyl isoureas; treatment with diazomethane or diazophenylmethane ($C_6H_5CHN_2$); by alcoholysis of anhydride derived from the cephalosporin acid corresponding to formula I; by transesterification with t-butyl esters or isopropenylacetate.

Other specific synthetic routes useful to prepare the compounds of formula I are described in U.S. Pat. Nos. 4,637,999; 5,446,037; 5,364,848 and U.S. patent application Ser. No. 08/354,850, filed Dec. 9, 1994. These synthetic methods are herein incorporated by reference.

The compounds of formula I have anti-inflammatory and anti-degeneratory activity due to their ability to inhibit the enzyme human leukocyte elastase as shown in Table 1, where PPE is porcine pancreatic elastase.

TABLE 1

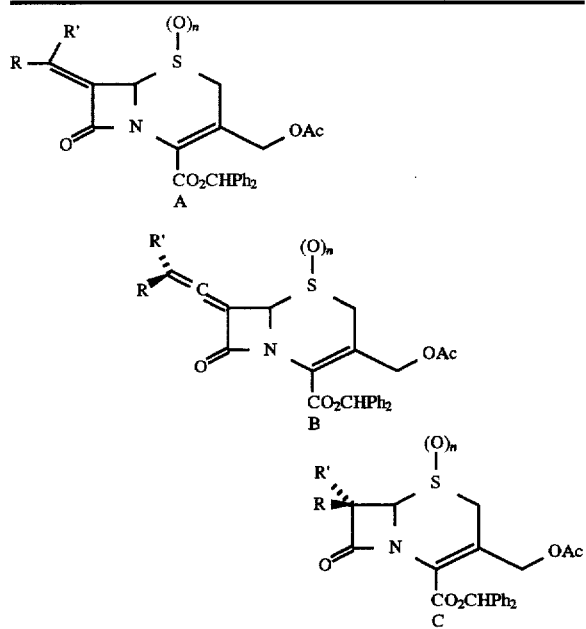

| Structure | Type | R | R' | n | IC₅₀(µM) PPE | HLE |
|---|---|---|---|---|---|---|
| 1 | C | NH₂ | H | 0 | >10 | >10 |
| 2 | C (Ketone) | | O | 0 | >10 | >10 |
| 4 | B | H | t-Bu | 0 | 5.5 | >10 |
| 5a | B | H | t-Bu | 2 | >10 | 10.5 |
| 5b | B | D | t-Bu | 2 | NT | 13.5 |
| 6 | B | H | Br | 0 | >10 | 5.4 |
| 7 | B | H | H | 0 | 0.67 | 9.0 |
| 8 | B | H | H | 2 | 4.1 | 6.1 |
| 9 | A | H | Ph | 0 | >10 | >10 |
| 10 | A | H | Ph | 2 | >10 | 8.9 |
| 11 | A | Ph | H | 0 | >10 | >10 |
| 12 | A | Ph | H | 2 | >10 | 6.0 |
| 13 | A | Br | Br | 0 | 6.42 | 0.26 |
| 14 | A | Br | Br | 2 | 4.8 | 2.07 |
| 15 | A | Br | H | 0 | 9.6 | 0.39 |
| 16 | A | Br | H | 2 | 2.49 | 3.36 |
| 17 | A | H | CO₂C(CH₃)₃ | 0 | NT | >10 |
| 18 | A | H | CO₂C(CH₃)₃ | 2 | >10 | 7.1 |
| 19 | A | H | CHO | 0 | 5.2 | 13.9 |
| 20 | A | H | 2'-Py | 0 | >10 | >10 |
| 21 | A | H | 2'Py | 2 | >10 | >10 |
| 22 | A | Cl | Cl | 0 | >10 | 6.41 |
| 23 | A | Cl | Cl | 2 | >10 | 2.56 |
| 24 | A | H | CO₂Me | 0 | >10 | 2.6 |
| 25 | A | H | CO₂Me | 2 | >10 | 8.9 |
| 26 | A | H | CH₂OH | 0 | >10 | >10 |
| 27 | A | H | CON(OMe)(Me) | 2 | >10 | >10 |
| 28 | A | H | COCH₃ | 0 | >10 | 4.27 |
| 29 | A | H | COCH₃ | 2 | 6.00 | >10 |
| 30 | A | H | CN | 0 | NT | >10 |
| 31 | A | H | CN | 2 | NT | 0.49 |
| 32 | A | Br | CO₂Me | 0 | NT | 0.21 |
| 33 | C | H | H | 0 | >10 | >10 |
| 34 | C | H | I | 0 | 5.6 | 1.18 |
| 35 | C | H | Cl | 0 | 2.9 | 6.0 |
| 36 | C | H | OMe | 0 | NT | 5.35 |
| 37 | C | H | OMe | 2 | NT | 0.28 |
| 38 | C | Br | Br | 0 | NT | 1.39 |
| 39 | N-(Methoxysuccinyl)-L-ala-L-ala-L-prol-L-val chloromethyl Ketone | | | | | 0.50 |

These IC₅₀ results represent the amount of inhibitor necessary to cause the enzyme to lose 50% of its activity after a 5 min incubation with the inhibitor. For comparison, a few of the compounds of structure C, prepared by Doherty (Doherty et. al., *J. Med. Chem.*, 33, 2513, 1990), and the allenes prepared by Buynak (Buynak et. al., *J. Am. Chem. Soc.*, 116, 10955, 1994) were also synthesized and tested. Compound 39, a commercially available, potent elastase inhibitor is also included.

In several cases, the activity of the compounds of formula A exceed those of formula C. The presence of the exocyclic double bond at position 7 is critical to the activity of these materials and dramatically affects their biological activity. For example, compounds of formula C typically show activity as the sulfur is in the sulfone oxidation state (n=2). By contrast, several compounds of formula A show activity when the compound is in the sulfide oxidation state (n=0).

To further document the rapid, irreversible inhibition of this enzyme at low, nearly stoichiometric ratios of inhibitor to enzyme, for selected compounds, this inhibition was followed as a function of time. The results of this study are shown in FIG. 1.

The data in FIG. 1 were generated by incubating the enzyme with a 10-fold molar excess of inhibitor. Assays of residual enzymatic activity of this mixture were assayed at regular intervals (2 to 5 minutes).

This data indicates that compound 13, in particular, is an extremely rapid and efficient inhibitor of HLE. It also indicates that several other members of this class also show substantial activity. In particular, compounds 15, 22, 24, and 14 all appear to be very potent, irreversible inhibitors of HLE. This is evident by the fact that inhibition with these compounds continues to increase (i.e., enzymatic activity decreases) as a function of time (rather than leveling off and allowing the enzyme to regain its activity, as is seen for compounds 16 and 28). For comparison, it should be noted that some current pharmaceutical products (for example, several commercial b-lactamase inhibitors, such as clavulanic acid) must be used at ratios of more than 200 to 1.

ADMINISTRATION AND DOSAGES

While it is possible that, for use in therapy, the compound(s) of formula I may be administered as the pure chemicals, as by inhalation of a fine powder via an insufflator, it is preferable to present the active ingredient as a pharmaceutical formulation. The invention thus further provides a pharmaceutical formulation comprising a compound of formula (I) and/or a pharmaceutically acceptable salt thereof, together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof, such as a human patient or domestic animal.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient; as a powder or as granules; as a solution, a suspension or as an emulsion; or in a chewable base such as a synthetic resin or chicle for ingestion of the cotinine from a chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampules, pre-filled syringes, small volume infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122; 4,383,529; or 4,051,842.

Formulations suitable for topical administration in the mouth include unit dosage forms such as lozenges comprising active ingredient in a flavored base, usually sucrose and acadia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described formulations can be adapted to give sustained release of the active ingredient employed, e.g., by combination with certain hydrophilic polymer matrices, e.g., comprising natural gels, synthetic polymer gels or mixtures thereof.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the compounds of the invention may be administered via a liquid spray, such as via a plastic bottle atomizer. Typical of these are the Mistometer® (Wintrop) and the Medihaler® (Riker).

For topical administration to the eye, the compounds can be administered as drops, gels (see, S. Chrai et al., U.S. Pat. No. 4,255,415), gums (see S. -L. Lin et al., U.S. Pat. No. 4,136,177) or via a prolonged-released ocular insert (see A. S. Michaels, U.S. Pat. No. 3,867,519 and H. M. Haddad et al., U.S. Pat. No. 3,870,791).

The pharmaceutical compositions according to the invention may also contain other adjuvants such as flavorings, colorings, antimicrobial agents, or preservatives.

It will be further appreciated that the amount of the compound of formula (I), or an active salt or derivative thereof, required for use in treatment will vary not only with the particular salt selected by also with the route of administration, the nature of the condition being treated and the age and condition of the patient and will be ultimately at the discretion of the attendant physician or clinician.

Dosage levels of active ingredient(s) can be based on the dosages disclosed to be effective in Maiti et al. (U.S. Pat. No. 5,446,037), Doherty et al. (U.S. Pat. No. 4,637,999), and P. E. Finke et al., *J. Med. Chem.*, 35, 3732 (1992). For example, the order to 0.2 mg to 150 mg per kilogram of body weight per day are useful in the treatment of the above-indicated conditions (about 10 mg to 9 gms per patient per day). For example, inflammation is effectively treated and anti-pyretic and analgesic activity manifested by the administration from about 0.5 to 50 mg of the compound per kilogram of body weight per day (25 mg to 3.5 gms per patients per day). Advantageously, from about 2 mg to about 20 mg per kilogram of body weight per daily dosage produces highly effective results (50 mg to 1 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

Pathologies associated with HLE are summarized in Table 3, below. The compounds of formula I can be used to treat these pathologies when formulated and administered as described hereinabove, i.e., to ameliorate at least some of the symptoms of these conditions, or to inhibit progression of the disease.

TABLE 3

HLE-Associated Pathologies

| Pathology | Reference |
|---|---|
| Pulmonary emphysema | G. Weinbaum et al., Ann. N.Y. Acad. Sci., 624, 45 (1991). |
| Cystic fibrosis | A. H. Jackson, J. Respir. Dis., 65, 114 (1984). |
| Chronic bronchitis | R. A. Stockley et al., Ann. N.Y. Acad. Sci., 624, 257 (1991). |
| Acute respiratory distress syndrome | T. A. Merritt et al., J. Clin. Invest., 72, 656 (1983). |
| Rheumatoid arthritis | E. O. Adeyemi et al., B. J. Rheumatol., 29, 15 (1990). |
| Septicemia | A. Janoff et al., Am. Rev. Respir. Dis., 132, 417 (1985). |
| Systemic lupus erythematosus | E. O. Adeyemi et al., B. J. Rheumatol., 29, 15 (1990). |
| Acute pancreatitis | U. Gross et al., Dig. Dis. Sci., 35, 97 (1990). |
| Inflammatory bowel disease | E. O. Adeyemi et al., Gut, 26, 1306 (1985). |
| Acute promyelocytic leukemia | M. Jochuss et al., In: Related Topics in Clinical Enzymology, D. A. Godberg et al. (eds.), pp. 85–100, Walter de Gruyter Co., Berlin, NY 1983. |
| Bronchopulmonary dysplasia | P. Birrer et al., In: Update on Childhood Asthma, Birkhauer-Verlag, Basel, pp. 3–12 (1993). |
| Lung destruction in patients with bronchiectasis | R. A. Stockley et al., Thorax, 39, 408 (1989). |
| Tissue destruction associated with ischemia/reperfusion of the intestinal mucosa | P. Kube et al., Drug News & Perspectives, 4, 197 (1992). |
| Inflammatory disease of the renal glomerulus | M. C. M. Visserts, Biochem. Biophy. Acta, 804, 154 (1984). |
| Atopic dermatitis | A. M. Wachter et al., Ann. Allergy, 69, 407 (1992). |
| Primary breast cancer recurrence | J. Yamashita et al., J. Leukoc. Biol, 57, 3 (1995). |
| Thrombotic thrombocytopenic purpura | M. Galbusesa et al., Lancet, 345, 224 (1995). |
| Behcet's disease | O. Deger et al., Clin. Chim. Acta, 236, 129 (1995). |
| Coronary artery disease | A. Amaro et al., Eur. Heart J., 16, 615 (1995). |
| Acute pyelonephritis | M. Morgan et al., Pediatr. Nephrol., 9, 583 (1995). |
| Tumor invasiveness in non-small cell lung cancer | J. Yamashita et al., Chest 109, 1328 (1996). |
| Chronic obstructive pulmonary disease | C. M. Sanguinetti, Respiration, 59, 20 (1992). |
| Chronic suppurative otitis media | Y. Itamaguchi et al., Ann. Otol. Rhinol. Laryngol. Supp., 157, 26 (1992). |
| Idiopathic pulmonary fibrosis | K. Kusume, Nippon Kyobu, Shikka Gakkai Zasshi, 29, 1254 (1991). |
| Chronic sinusitis | Y. Hamaguchi et al., Acta Otolaryngol. (Stockh), 111, 954 (1991). |
| Contact dermatitis and psoriasis | O. Wiedow, J. Invest. Dermatol, 99, 306 (1992). |
| Normal and chronic granulomatous disease | S. S. Weiss et al., J. Immunol., 136, 636 (1986). |

The invention will be further described by reference to the following detailed examples, wherein all assays of elastase activity were performed on a Beckman DU-650 spectrophotometer, and hydrolysis rates of the elastase substrate, N-(methoxysuccinyl)-L-alanyl-L-alanyl-L-prolyl-L-valine 4-nitroanilide, were monitored at 410 nm. This substrate was purchased from Fluka Chemical Corporation (Ronkonkoma, N.Y.). Melting points are uncorrected and determined on a MEL-TEMP capillary melting point apparatus. Infrared spectra were recorded on a Perkin-Elmer Model 710B diffraction grating spectrophotometer or a Perkin-Elmer 1600 Series Fourier transform infrared spectrophotometer. $^1$H and $^{13}$C NMR spectra were recorded on a Bruker WP200SY spectrometer. Proton chemical shifts are reported in parts per million ($\delta$) downfield from tetramethylsilane (0.0). Carbon chemical shifts are reported in parts per million ($\delta$) by using d-chloroform (77.0) as the reference. Elemental analyses were performed by Galbraith Laboratories, Knoxville, Tenn. Mass spectral data were obtained by FAB techniques from the Midwest Center for Mass Spectrometry at the University of Nebraska-Lincoln, Lincoln, Nebr. Thin layer chromatography (TLC) was performed on Merck 0.2 mm Kieselgel 60 $F_{254}$ silica-coated aluminum plates.

The compounds were identified in one or more of the following manners: UV (254 nm), iodine chamber and/or phosphomolybdic acid spray reagent. The position of the compounds on the TLC plate are listed as an $R_f$ value in the given solvent(s). Flash chromatography was performed by using thick-walled glass columns and Merck's 0.040–0.063 mm Kieselgel 60 silica gel. The (flash) chromatography solvents were distilled from calcium hydride before use. All additional solvents were obtained from Aldrich in Sure-Seal bottles.

HLE was purchased from Elastin Products Company, Inc. (Owensville, Mo.). Trizma Base and Trizma Hydrochloride were both obtained from Sigma Chemical Company (St. Louis, Mo.). All other reagents were used as received from Aldrich unless otherwise noted. Unless otherwise specified, all yields refer to the isolation of purified material (after chromatography).

For $IC_{50}$ determinations, the 0.1M Tris-NaCl buffer solution of pH 7.5 was prepared by dissolving 12.7 g of Tris-HCl, 2.36 g of Tris-base, 29.22 g of NaCl and 0.1 g of $NaN_3$ in 900 mL of $H_2O$. The pH was determined and was brought to 7.5 at 25° C. with 0.1M HCl or 0.1M NaOH, if necessary. The volume was increased to 1000 mL with water. The NaOAc—NaCl buffer was prepared by combining 0.2M HOAc (14.8 mL), 0.2M NaOAc (35.2 mL), and 100 mL of 0.2M NaCl. 0.1 g of $NaN_3$ was added and the volume was brought to 200 mL with water. The Human Leukocyte Elastase solution was prepared by adding HLE (0.36 mg) to 1 mL of NaCl—NaOAc Buffer. The inhibitor solutions were prepared by dissolving 1 mg of the specified inhibitor in 1 mL of DMSO. With exceptionally good inhibitors, dilutions of this solution were made by taking 10 uL of the inhibitor solution and increasing the volume to 100 uL with DMSO.

For the determination of the $IC_{50}$, a specified volume (0–20 uL) of the inhibitor solution was diluted with 20 uL Tris Buffer and enough DMSO to bring the total volume to 40 uL. Then 10 uL of the elastase solution was added and the mixture allowed to incubate for 4 minutes. 40 uL of this solution was then withdrawn and added to a solution of 50 uL of substrate solution in 900 uL of Tris Buffer. The hydrolysis rate of the substrate was determined spectrophotometrically by monitoring the absorbance at 410 nm for 2 minutes at 1 second intervals.

Compounds 33–38 were synthesized for comparison purposes only as described by Doherty (Doherty et. al. *J Med. Chem.*, 33, 2513, 1990).

EXAMPLE 1

Benzhydryl 7β-aminocephalosporanate (1).

To a suspension of 7-aminocephalosporanic acid (130.4 g, 0.48 mol) in methanol (480 mL) was added a solution of diphenyldiazomethane (93.0 g, 0.48 mol) in $CH_2Cl_2$. The reaction was then mechanically stirred at rt for 44 h. The remaining solid was removed by filtration. The resultant filtrate was concentrated in vacuo and purified by column chromatography (10% $CH_3OH$ in $CH_2Cl_2$) to afford the desired ester as pale yellow solid (86.1 g, 41% yield). $R_f$=0.44 in 1:9 $CH_3OH:CH_2Cl_2$; mp. 45°–46° C.; IR (CHCl$_3$) 2980, 1780, 1730 cm$^{-1}$; $^1H$ NMR (CDCl$_3$) δ 8.41 (2H, bs), 7.22 (10H, m), 6.91 (1H, s), 5.27 (1H, d, J=2.8 Hz), 5.15 (1H, d, A of ABq, J=14 Hz), 4.94 (1H, s), 4.84 (1H, d, B of ABq, J=14 Hz), 3.73 (1H, d, A of ABq, J=17 Hz), 3.33 (1H, d, B of ABq, J=17 Hz), 1.92 (3H, s); $^{13}C$ NMR (CDCl$_3$) δ 169.8, 168.8, 160.6, 138.9, 138.7, 129.5, 129.3, 129.1, 128.7, 128.5, 127.97, 127.61, 127.52, 127.18, 126.52, 126.06, 125.4, 79.0, 63.3, 62.6, 58.5, 25.7, 20.1.

EXAMPLE 2

Benzhydryl 7-oxocephalosporanate (2)

The title compound was prepared by modifying the procedure of Hagiwara et al. (*J Chem. Soc., Chem. Commun.* 578, 1982). To a solution of benzhydryl 7β-aminocephalosporanate, (5.9 g, 13.5 mmol) in anhydrous $CH_2Cl_2$ (70 mL) at −78° C., triethylamine (5.6 mL, 40.4 mmol) was added dropwise with stirring. After 5 min, trifluoromethanesulfonic anhydride (6.8 mL, 40.4 mmol) was added dropwise to this solution over a 5 minute period. The reaction mixture was allowed to warm slowly to 0° C. over a 1 h period. It was then recooled to −78° C. and triethylamine (5.6 mL, 40.4 mmol) was added over approximately 10 min. The reaction mixture was stirred at −78° C. for an additional 30 min and poured into 200 mL cold 0.5N HCl. The resultant mixture was further stirred until the ice melted. The layers were separated and the aqueous layer was extracted with $CH_2Cl_2$ (150 mL). The combined organic layers were washed with cold 0.5N HCl (3×100 mL), dried ($Na_2SO_4$), and concentrated (at room temperature or below) to produce the title compound (5.8 g, 98% yield) as a brown solid which was used without further purification. IR (CHCl$_3$) 3005, 1830, 1790, 1740 cm$^{-1}$; $^1H$ NMR (CDCl$_3$) δ 7.39 (10H, m), 7.05 (1H, s), 5.32 (1H, s), 5.07 (1H, d, A of ABq, J=14 Hz), 4.85 (1H, d, B of ABq, J=14 Hz), 3.64 (1H, d, A of ABq, J=18 Hz), 3.44 (1H, d, B of ABq, J=18 Hz), 2.05 (3H, s); $^{13}C$ NMR (CDCl$_3$) δ 188.4 (s), 170.3 (s), 160.1 (s), 158.7 (s), 138.8 (s), 138.6 (s), 128.4, 128.2, 128.1, 127.7, 126.9, 126.2, 80.1 (d), 65.8 (d), 62.6 (t), 27.7 (t), 20.4 (q).

EXAMPLE 3

Benzhydryl 6-ethynyl-6-hydroxycephalosporanate

Ethynylmagnesium bromide (45.2 mL, 22.6 mmol) was slowly added to the cold (−78° C.) solution of 7-oxocephalosporanate (2) (5.5 g, 12.6) in anhydrous THF (85 mL). It was then further stirred at −78° C. for 1 h and at −40° C. for 1 h 30 min. The reaction mixture was then quenched with acetic acid (2.9 mL, 50.4 mmol) and the product was extracted with ether (2x, 100 mL). The combined organic layers were washed with water (1x, 30 mL), brine (1x, 30 mL), dried ($Na_2SO_4$), and concentrated in vacuo. It was then purified by column chromatography (1:4 EtOAc:$CH_2Cl_2$) to give the title compound (2.9 g, 50% yield) as pale yellowish fluffy solid. $R_f$=0.56 in 1:4 EtOAc:$CH_2Cl_2$ mp. 50°–52° C. IR (CHCl$_3$) 3670, 3565, 3300, 3010, 2120, 1790, 1730 cm$^{-1}$. $^1H$ NMR (CDCl$_3$) 7.37 (10H, m), 6.95 (1H, s), 5.14(1H, d, A of ABq, J=13.9 Hz), 5.08 (1H, s), 4.89 (1H, d, B of ABq, J=13.9 Hz), 3.53 (1H, d, A of ABq, J=17.8 Hz), 3.35 (1H, d, B of ABq, J=17.8 Hz), 2.88 (1H, s), 2.05 (3H, s). $^{13}C$ NMR (CDCl$_3$) 170.7 (s), 162.7 (s), 160.3 (s), 139.3 (s), 139.1 (s), 132.1 (s), 128.42, 128.0, 127.3, 126.9, 125.6, 79.6 (d), 78.3 (s), 77.9 (s), 77.3 (d), 65.4 (d), 62.6 (t), 26.3 (t), 20.5 (q). Analysis Calcd for $C_{25}H_{21}NO_6S$: C, 64.79; H, 4.54; N, 3.02. Found: C, 64.20; H, 4.39; N, 3.25. Two more compounds were isolated from this reaction and they are: 1. Benzhydryl 6β-ethynyl-6α-hydroxycephalosporinate. Yellow solid (0.58 g, 10% yield). $R_f$=0.041 in 1:4 EtOAc:$CH_2Cl_2$. IR (CHCl$_3$) 3550, 3300, 3010, 2105, 1780, 1735 cm$^{-1}$. $^1H$ NMR (CDCl$_3$) 7.34 (10H, m), 6.92 (1H, s), 6.45 (1H, d, J=1.3 Hz), 5.30 (1H, s), 5.19 (1H, d, J=1.3 Hz), 4.63 (2H, s), 2.80 (1H, s), 2.05 (OH, s), 1.99 (3H, s). $^{13}C$ NMR (CDCl$_3$) 170.7 (s), 165.6 (s), 162.8 (s), 138.8 (s), 128.5, 128.2, 127.6, 127.4, 126.8, 126.6, 122.1 (d), 119.2 (s), 78.9 (s), 78.8 (d), 77.6 (d), 76.9 (s), 65.5 (t), 61.0 (d), 50.2 (d), 20.4 (q). 2. Benzhydryl 6-hydroxycephalosporanate. pale yellow solid (0.59 g, 10% yield). $R_f$=0.26 in 1:4 EtOAc:$CH_2Cl_2$. IR (CHCl$_3$) 3680, 3350, 3010, 1795, 1735 cm$^{-1}$. $^1H$ NMR (CDCl$_3$) 7.38 (10H, m), 6.93 (1H, s), 5.39 (1H, d, J=4.9 Hz), 5.15 (1H, d, A of ABq, J=13.8 Hz), 4.97 (1H, d, J=4.8 Hz), 4.81 (1H, d, B of ABq, J=13.8 Hz), 3.57 (1H, d, A of ABq, J=18.6 Hz), 3.39 (1H, d, B of ABq, J=18.7 Hz), 2.16 (OH, s), 2.04(3H, s). $^{13}C$ NMR (CDCl$_3$) 170.7 (s), 162.5 (s), 160.3 (s), 139.0 (s), 138.7 (s), 129.4, 128.5, 128.4, 128.3, 128.1, 127.7, 127.0, 80.0 (d), 62.4 (d), 57.2 (d), 26.3 (t), 20.4 (q).

EXAMPLE 4

Benzhydryl 6-ethynyl-6-trifluoromethanesulfonatocephalosporanate (3)

Trifluoromethanesulfonic anhydride (3.3 mL, 19.1 mmol) was added dropwise (4 s intervals) to a cold (0° C.) solution of pyridine (2.6 mL, 31.8 mmol) and benzhydryl 6-ethynyl-6-hydroxycephalosporanate (5.9 g, 12.7 mmol) in anhydrous $CH_2Cl_2$(60 mL). The reaction mixture was allowed to warm to rt and monitored by TLC (reaction time=30 min). After concentration the residue was purified by column chromatography ($CH_2Cl_2$) to yield the title compound as a white solid (4.67 g, 62% yield). $R_f$=0.63 in 15% EtOAc in $CH_2Cl_2$. mp 42°–43° C. IR (CHCl$_3$) 3300, 3020, 2120, 1810, 1780, 1750 cm$^{-1}$. $^1H$ NMR (CDCl$_3$) 7.39 (10H, m), 6.94 (1H, s), 5.29 (1H, d, A of ABq, J=13.9 Hz), 5.26 (1H, s), 5.09 (1H, d, B of ABq, J=14.8 Hz), 3.52 (1H, d, A of ABq, J=16.5 Hz), 3.34 (1H, d, B of ABq, J=18.3 Hz), 3.29 (1H, s), 2.09 (3H, s). $^{13}C$ NMR (CDCl$_3$) 170.1 (s), 159.4(s), 155.1 (s), 140.8 (s), 139.2 (s), 139.1 (s), 128.5, 128.1, 126.9, 126.8, 125.3, 118.0 (q, J=321.11 Hz), 87.3 (s), 84.0 (d), 79.6 (d), 71.9 (s), 66.5 (d), 61.7 (t), 26.5 (t), 20.4 (q). Analysis Calcd. for $C_{26}H_{20}NO_8S_2F_3$: C, 52.44; H, 3.36; N, 2.35; F, 9.58. Found: C, 52.66; H, 3.37; N, 2.33; F, 9.26.

EXAMPLE 5

Benzhydryl 7-(t-butylvinylidene)cephalosporanate (4)

To a suspension of CuCN (0.376 g, 4.2 mmol) in anhydrous THF (30 mL) was added t-BuLi (4.0 mL, 6.8 mmol) at −100° C. The cooling bath was removed until all the solid had gone into the solution (approximately 3 min). This solution was again cooled to −100° C. and was cannulated into a cold solution of benzhydryl 6-ethynyl-6-trifluoromethanesulfonatocephalosporanate (3) (2.0 g, 3.4 mmol) in anhydrous THF (5 mL) at −100° C. The solution was further stirred at −100° C. for 1 min before quenching with saturated $NH_4Cl$ solution. The reaction mixture was extracted with ether (2x, 50 mL), dried ($Na_2SO_4$) and concentrated and chromatographed (5% EtOAc in $CH_2Cl_2$) to give white fluffy solid (0.913 g, 54% yield). $R_f$=0.80 in 5% EtOAc in $CH_2Cl_2$. mp 113°–114° C. IR ($CHCl_3$) 3000, 2960, 1970, 1770, 1730 $cm^{-1}$. $^1H$ NMR ($CDCl_3$) 7.42 (10H, m), 7.05 (1H, s), 5.98 (1H, d, J=1.63 Hz), 5.25 ( 1H, d, J=1.69 Hz), 4.97 (1H, d, A of ABq, J=13.30 Hz), 4.72 ( 1H, d, B of ABq, J=13.23 Hz), 3.55 (1H, d, A of ABq, J=18.14 Hz), 3.35 (1H, d, B of ABq, J=18.23 Hz), 2.01 (3H, s), 1.18 (9H, s). $^{13}C$ NMR ($CDCl_3$) 194.6 (s), 170.2 (s), 161.1 (s), 159.5 (s), 139.2 (s), 139.0 (s), 128.3,128.0,127.9, 127.7, 127.1, 121.9, 113.2 (d), 107.2 (s), 79.6 (d), 63.0 (t), 57.0 (d), 33.6 (s), 29.7 (q), 27.8 (t), 20.5 (q). Analysis Calcd. for $C_{29}H_{29}NO_5S$: C, 69.18; H, 5.77; N, 2.78. Found: C, 69.08; H, 6.00; N, 2.73.

EXAMPLE 6

Benzhydryl 7-t-butylvinylidene cephalosporanate sulfone (5)

General Procedure for the Preparation of Cephalosporin Sulfones

To a solution of sulfide 4 (0.252 g, 0.5 mmol) in $CH_2Cl_2$ (10 mL) and pH=6.4 Buffer solution (10 mL) was added m-CPBA (85%, 0.35 g, 2.0 mmol) in one portion. The mixture was stirred at rt for 40 min, and then ether (50 mL) was added. After separating layers, the organic layers were washed with saturated $NaHCO_3$ (3×30 mL), dried ($NaSO_4$), concentrated and purified by column chromatography to yield a white solid (yield=65%, 0.174 g). $R_f$=0.42 in 2% EtOAc in $CH_2Cl_2$. mp 163°–164° C. IR ($CHCl_3$) 3010, 2960, 1970, 1790, 1740, 1340, 1125 $cm^{-1}$. $^1H$ NMR ($CDCl_3$) 7.40 (10H, m), 7.01 (1H, s), 6.18 (1H, d, J=1.66 Hz), 5.30 (1H, s), 5.02 (1H, d, A of ABq, J=13.93 Hz), 4.68 (1H, d, B of ABq, J=13.93 Hz), 4.02 (1H, d, A of ABq, J=18.27 Hz), 3.76 (1H, d, B of ABq, J=18.20 Hz), 2.03 (3H, s), 1.19 (9H, s). $^{13}C$ NMR ($CDCl_3$) 197.1 (s), 170.1 (s), 160.0 (s), 158.6 (s), 138.8 (s), 138.7 (s), 128.5, 128.3, 128.2, 127.6, 127.1, 126.5, 123.1, 114.6 (d), 100.1 (s), 80.4 (d), 70.1 (d), 62.0 (t), 51.2 (t), 34.0 (s), 29.7 (q), 20.4 (q). Analysis Calcd. for $C_{29}H_{29}NO_7S$: C, 65.05; H, 5.42; N, 2.62. Found: C, 63.27; H, 5.30; N, 2.43.

EXAMPLE 7

Benzhydryl 7-(-bromovinylidene)cephalosporanate (6)

Method A: Copper (I) bromide (CuBr, 133 mg, 0.93 mmol) was added in one portion to a solution of benzhydryl 6-ethynyl-6-(trifluoromethanesulfonato)cephalosporanate (500 mg, 0.84 mmol) in anhydrous DMF (5.0 mL) at rt and stirred in the dark for 30 min. The DMF was removed in vacuo at rt. The residue was dissolved in ether (50 mL), washed with water (2x, 15 mL), dried ($Na_2SO_4$), and concentrated to give yellow solid. This material was purified by column chromatography ($CH_2Cl_2$) to yield title compound as pale yellow solid (140 mg, 32% yield). $R_f$=0.75 in 15% EtOAc in $CH_2Cl_2$. mp 63-65 °C. IR ($CHCl_3$) 3010, 1950, 1780, 1730 $cm^{-1}$. $^1H$ NMR ($CDCl_3$) 7.42 (10H, m), 7.01 (1H, s), 6.74 (1H, d, J=1.17 Hz), 5.38 (1H, d, J=1.12 Hz), 5.02 (1H, d, A of ABq, J=13.5 Hz), 4.78 (1H, d, B of ABq, J=13.4 Hz), 3.60 (1H, d, A of ABq, J=18.31 Hz), 3.41 (1H, d, B of ABq, J=18.11 Hz), 2.04 (3H, s). $^{13}C$ NMR ($CDCl_3$) 194.6 (s), 170.3 (s), 160.6 (s), 156.1 (s), 139.1 (s), 138.9 (s), 128.4, 128.1, 128.0, 127.7, 127.1, 124.6, 111.7 (s), 81.8 (d), 79.9 (d), 62.9 (t), 56.2 (d), 27.8(t), 20.5 (q). Method B: Lithium bromide (LiBr, 285 mg, 3.3 mmol), and copper (I) bromide (CuBr, 470 mg, 3.3 mmol) were added in one portion to a solution of benzhydryl 6-ethynyl-6-trifluoromethanesulfonato-cephalosporanate (1.5 g, 2.5 mmol) in anhydrous THF (15 mL). The mixture was allowed to stir at rt for 5 min. The THF was removed in vacuo. The residue was dissolved in ether (20 mL), washed with water (1x, 10 mL), dried ($Na_2SO_4$), and concentrated in vacuo to give yellow solid (1.30 g, 98% yield).

EXAMPLE 8

Benzhydryl 7-vinylidenecephalosporanate (7)

To a solution of benzhydryl 7-(-bromovinylidene) cephalosporanate (2.4 g, 4.6 mmol) in a 1:5 mixture of anhydrous THF:MeOH (60 mL) was added $NH_4Cl$ (0.98 g, 18.4 mmol) and Zn—Cu couple (0.6 g, 9.2 mmol). After stirring at rt for 30 min, the reaction mixture was concentrated. The residue was dissolved in ether (100 mL), washed with water (20 mL), dried ($Na_2SO_4$), concentrated, and chromatographed (1:1 Hexane: $CH_2Cl_2$ and 1:3 Hexane: $CH_2Cl_2$) to give white fluffy solid ( 1.45 g, 71% yield). $R_f$=0.3 in $CH_2Cl_2$. IR ($CHCl_3$) 3010, 1985, 1790, 1730 $cm^{-1}$. $^1H$ NMR ($CDCl_3$) 7.40 (10H, m), 7.0 (1H, s), 5.58 (2H, d, J=13.4 Hz), 5.29 (1H, t, J=1.88 Hz), 4.99 (1H, d, A of ABq, J=13.35 Hz), 4.74 (1H, d, B of ABq, J=13.3 Hz), 3.57 (1H, d, A of ABq, J=18.2 Hz), 3.37 (1H, d, B of ABq, J=18.3 Hz), 2.03 (3H, s). $^{13}C$ NMR ($CDCl_3$) 200.0 (s), 170.3 (s), 160.8 (s), 158.7 (s), 139.2 (s), 139.0 (s), 128.4, 128.0, 127.9, 127.7, 127.4, 127.0, 123.0, 105.7 (s), 85.1 (t), 79.7 (d), 63.0 (t), 56.6 (d), 27.8 (t), 20.5 (q). Analysis Calcd. for $C_{25}H_{21}NO_5S$: C, 67.11; H, 4.70; N, 3.13. Found: C, 66.02; H, 4.69; N, 3.03.

EXAMPLE 9

Benzhydryl 7-vinylidenecephalosporanate sulfone (8)

This compound was prepared from the sulfide 7 as described above for the preparation of 5 (yield=55%, 0.590 g). $R_f$=0.35 in 5% EtOAc in $CH_2Cl_2$. mp 155°–156° C. IR ($CHCl_3$) 3010, 1985, 1790, 1730, 1340, 1125 $cm^{-1}$. $^1H$ NMR ($CDCl_3$) 7.43 (10H, m), 6.99 (1H, s), 5.70 (2H, dd, J=1.65 Hz, J=5.31 Hz), 5.33 (1H, s), 5.03 (1H, d, A of ABq, J=14.02 Hz), 4.70 (1H, d, B of ABq, J=14.01 Hz), 4.04 (1H, d, A of ABq, J=18.12 Hz), 3.79 (1H, d, B of ABq, J=18.40 Hz), 2.03 (3H, s). $^{13}C$ NMR ($CDCl_3$) 201.7 (s), 170.1 (s), 159.8 (s), 157.6 (s), 138.8 (s), 138.6 (s), 128.4, 128.2, 128.1, 127.5, 127.0, 124.0, 98.8 (s), 86.4 (t), 80.3 (d), 69.5 (d), 61.9 (t), 51.0 (t), 20.3 (q). Analysis Calcd. for $C_{25}H_{21}NO_7S$: C, 62.63; H, 4.38; N, 2.92. Found: C, 59.22; H, 4.19; N, 2.58.

EXAMPLE 10

Benzhydryl 7-[(E)-benzylidene]cephalosporanate (11) and benzhydryl 7-[(Z)-benzylidene] cephalosporanate (9)

To a solution of benzyl triphenylphosphonium bromide (11.44 g, 26.4 mmol) in anhydrous THF (50 mL) was added a solution of n-BuLi (14.5 mL, 29.0 mmol) at −78° C. The mixture was stirred at rt for 30 min. The resulting red colored solution was recooled to −78° C. and was added to a cold (−78° C. solution of 7-oxocephalosporanate 3 (10.5 g, 24.0 mmol) in anhydrous THF (25 mL) and stirred at −78° C. for 5 min. The cold reaction mixture was then poured into ice cold saturated $NH_4Cl$ solution (25 mL) and the layers were separated. The aqueous layer was extracted with ether (2×50 mL). The combined organic layers were washed with water (25 mL), dried ($Na_2SO_4$), concentrated and purified by column chromatography ($CH_2Cl_2$: Hexane, 3:1) to give the E-isomer (0.83 g, 7%), and the Z-isomer (1.26 g, 10%) as white fluffy solids.

7-(E)-isomer. $R_f$=0.60 in $CH_2Cl_2$; mp 59°–61° C.; IR (CHCl$_3$) 3015, 1760, 1730 cm$^{-1}$; $^1$H NMR (CDCl$_3$) δ 7.83 (2H, m), 7.26 (13H, m), 6.93 (1H, s), 6.53 (1H, s), 4.99 (1H, s), 4.78 (1H, d, A of ABq, J=13 Hz), 4.53 (1H, d, B of ABq, J=13 Hz), 3.39 (1H, d, A of ABq, J=18 Hz), 3.19 (1H, d, B of ABq, J=18 Hz), 1.85 (3H, s); $^{13}$C NMR (CDCl$_3$) δ 170.2 (s), 161.1 (s), 158.7 (s), 139.3 (s), 139.1 (s), 136.0(s), 134.0 (d), 133.1, 130.3, 128.6, 128.3, 128.0, 127.7, 127.0, 121.7 (s), 79.6 (d), 63.1 (t), 56.1 (d), 27.9 (t), 20.5 (q). Anal. ($C_{30}H_{25}NO_5S$) C, H, N.

7-(Z)-isomer. $R_f$=0.50 in $CH_2Cl_2$; mp 45°–47° C.; IR (CHCl$_3$) 3025, 1790, 1760 cm$^{-1}$; $^1$H NMR (CDCl$_3$) δ 7.43 (15H, m), 7.21 (1H, d, J=1.18 Hz), 7.07 (1H, s), 5.50 (1H, d, J=1.23 Hz), 5.00 (1H, d, A of ABq, J=13 Hz), 4.75 (1H, d, B of ABq, J=13 Hz), 3.65 (1H, d, A of ABq, J=18 Hz), 3.41 (1H, d, B of ABq, J=18 Hz), 2.04 (3H, s); $^{13}$C NMR (CDCl$_3$) δ 170.3 (s), 161.0 (s), 160.2 (s), 139.3 (s), 139.1 (s), 135.8(s), 132.4 (d), 130.5, 129.7, 129.0, 128.3, 128.1, 127.9, 127.7, 127.0, 121.7(s), 79.7 (d), 63.1 (t), 57.7 (d), 28.0 (t), 20.5 (q); high-resolution mass spectrum for [$C_{30}H_{25}NO_5SNa$]$^+$, i.e. [M+Na]$^+$, m/z calcd 534.1351, found 534.1352.

EXAMPLE 11

Benzhydryl 7-[(Z)-benzylidene]cephalosporanate sulfone (10)

This compound was prepared from the sulfide 9 (0.68 g, 1.3 mmol) as described for 5 to give a white solid (yield= 57%, 0.410 g). $R_f$=0.40 in $CH_2Cl_2$. mp 61°–63° C. IR (CHCl$_3$) 3025, 2925, 1780, 1730, 1340, 1130 cm$^{-1}$; $^1$H NMR (CDCl$_3$) δ 7.42 (15H, m), 7.12 (1H, s), 6.98 (1H, s), 5.53 (1H, s), 4.95 (1H, d, A of ABq, J=13 Hz), 4.65 (1H, d, B of ABq, J=13 Hz), 4.04 (1H, d, A of ABq, J=18 Hz), 3.77 (1H, d, B of ABq, J=18 Hz), 1.96 (3H, s); $^{13}$C NMR (CDCl$_3$) δ 170.1 (s), 159.9 (s), 159.7 (s), 138.8 (s), 138.7 (s), 134.12 (s), 131.6 (d), 131.0, 129.8, 129.1, 128.4, 128.2, 128.1, 127.6, 127.0, 126.7, 126.2, 121.8 (d), 80.3 (d), 71.7 (d), 691.9 (t), 51.6 (t), 20.3 (q); high-resolution mass spectrum for [$C_{30}H_{25}NO_7SNa$]$^+$, i.e. [M+Na]$^+$, m/z calcd 566.1249, found 566.1262.

EXAMPLE 12

Benzhydryl 7-[(E)-benzylidene]cephalosporanate sulfone (12)

This compound was prepared from the sulfide 11 (0.51 g, 1.0 mmol) as described for 5 to give a white solid (0.350 g, yield=65%, ). $R_f$=0.27 in $CH_2Cl_2$. mp 194°–196° C.; IR (CHCl$_3$) 2975, 1775, 1730, 1340, 1125 cm$^{-1}$; $^1$H NMR (CDCl$_3$) δ 8.00 (2H, m), 7.41 (13H, m), 7.03 (1H, s), 6.94 (1H, s), 5.24 (1H, s), 5.04 (1H, d, A of ABq, J=14 Hz), 4.70 (1H, d, B of ABq, J=14 Hz), 4.05 (1H, d, A of ABq, J=18 Hz), 3.77 (1H, d, B of ABq, J=18 Hz), 2.05 (3H, s). $^{13}$C NMR (CDCl$_3$) δ 170.3 (s), 160.1(s), 157.7 (s), 138.9 (s), 138.8 (s), 138.5(d), 132.5, 131.5, 131.0, 128.9, 128.6, 128.3, 127.7, 127.1, 126.7, 122.8 (s), 80.4 (d), 69.5 (d), 62.1 (t), 51.2 (t), 20.5 (q); high-resolution mass spectrum for [$C_{30}H_{25}NO_7SNa$]$^+$, i.e. [M+Na]$^+$, m/z calcd 566.1249, found 566.1248.

EXAMPLE 13

Benzhydryl 7-[dibromomethylene]cephalosporanate (13)

To the solution of Ph$_3$P (12.0 g, 45.8 mmol) in anhydrous $CH_2Cl_2$ (75 mL) was added CBr$_4$ (7.6 g, 22.9 mmol) in one portion at 0° C. The mixture was stirred at rt for 30 min. The reaction mixture was then cooled to −78° C. and a cold (−78° C.) solution of benzhydryl 7-oxocephalosporanate 3 (5.00 g, 11.4 mmol) in anhydrous $CH_2Cl_2$ (40 mL), was added. After stirring at −78° C. for 30 min, the reaction was concentrated in vacuo and purified by column chromatography ($CH_2Cl_2$) to give a pale yellow solid (4.1 g, 61% yield). $R_f$=0.55 in $CH_2Cl_2$; mp 58°–60° C.; IR (CHCl$_3$) 3030, 1780, 1745 cm$^{-1}$; $^1$H NMR (CDCl$_3$) δ 7.37 (10H, m), 6.96 (1H, s), 5.19 (1H, s), 4.97 (1H, d, A of ABq, J=13 Hz), 4.72 (1H, d, B of ABq, J=13 Hz), 3.52 (1H, d, A of ABq, J=18 Hz), 3.32 (1H, d, A of ABq, J=18 Hz), 2.00 (3H, s); $^{13}$C NMR (CDCl$_3$) δ 170.2 (s), 160.5 (s), 155.6 (s), 142.6 (s), 139.1 (s), 138.9 (s), 128.4, 128.0, 127.9, 127.0, 126.7, 125.2 (s), 92.6 (s), 79.9 (d), 63.0 (t), 60.1 (d), 27.0 (t), 20.5 (q). Anal. ($C_{24}H_{19}NO_5SBr_2$) C, H, N.

EXAMPLE 14

Benzhydryl 7-[dibromomethylene]cephalosporanate sulfone (14)

This compound was prepared from the sulfide 15 as described above for 5 to yield a white solid (0.25 g, 79%). $R_f$=0.50 in 2% EtOAc in $CH_2Cl_2$; mp 62°–64° C.; IR (CHCl$_3$) 3030, 1800, 1740, 1350, 1130 cm$^{-1}$ ; $^1$H NMR (CDCl$_3$) δ 7.36 (10H, m), 6.95 (1H, s), 5.20 (1H, s), 5.03 (1H, d, A of ABq, J=14 Hz), 4.68 (1H, d, B of ABq, J=14 Hz), 4.02 (1H, d, A of ABq, J=18 Hz), 3.77 (1H, d, B of ABq, J=18 Hz), 2.02 (3H, s); $^{13}$C NMR (CDCl$_3$) δ 170.1 (s), 159.6 (s), 154.8 (s), 138.8 (s), 138.7 (s), 135.2 (s), 128.6, 128.3, 127.5, 127.1, 126.4, 125.5 (s), 124.1(s), 98.2 (s), 80.8 (d), 73.0 (d), 62.0 (t), 52.1 (t), 20.5 (q). Anal. ($C_{24}H_{19}NO_7SBr_2$) C, H, N, Br.

EXAMPLE 15

Benzhydryl 7-[(E)-bromomethylene] cephalosporanate (15)

To a solution of 7-[dibromomethylene]cephalosporanate 13 (1.19 g, 2 mmol) in methanol (20 mL) and THF (10 mL) was added NH$_4$Cl (8.56 g, 16 mmol) in one portion at 0° C. The mixture was stirred for 5 min. Zn/Cu (5.20 g, 8 mmol) was added in one portion and further stirred at rt for 30 min. The solvent was removed, and residue was extracted with ether (2×20 mL). The obtained ether was washed with water (1×20 mL) and brine (1×10 mL), dried ($Na_2SO_4$), concentrated and purified by column chromatography ($CH_2Cl_2$) to give a white solid (0.86 g, 83% yield). $R_f$=0.41 in $CH_2Cl_2$; mp 48°–50° C.; IR (CHCl$_3$) 3025, 1780, 1730 cm$^{-1}$; $^1$H NMR (CDCl$_3$) δ 7.32 (10H, m), 6.96 (1H, s), 6.44 (1H, s), 5.05 (1H, s) 4.92 (1H, d, A of ABq, J=13 Hz), 4.67 (1H, d, B of ABq, J=13 Hz), 3.46 (1H, d, A of ABq, J=18 Hz), 3.26 (1H, d, B of ABq, J=18 Hz), 1.96 (3H, s); $^{13}$C NMR (CDCl$_3$) δ 170.15 (s), 160.60 (s), 157.04 (s), 141.77 (s), 139.05 (s), 138.86 (s), 128.32, 127.97, 127.89, 127.49, 126.92, 123.30 (s), 107.94 (d), 79.82 (d), 62.90 (t), 58.02 (d), 27.68 (t), 20.42 (q). Anal. ($C_{24}H_{20}NO_5SBr$) C, H, N.

EXAMPLE 16

Benzhydryl 7-[(E)-bromomethylene] cephalosporanate sulfone (16)

This compound was prepared from the corresponding sulfide 13 as described above for 5 to give a white solid (yield=71%). $R_f$=0.43 in 2% EtOAC in $CH_2Cl_2$; mp 80°–82° C.; IR (CHCl$_3$) 3030, 1800, 1730, 1350, 1130 cm$^{-1}$; $^1$H NMR (CDCl$_3$) δ 7.33 (10H, m), 6.94 (1H, s), 6.91 (1H, s), 5.10 (1H, s), 5.00 (1H, d, A of ABq, J=14 Hz), 4.67 (1H, d, B of ABq, J=14 Hz), 3.97 (1H, A of ABq, J=18 Hz), 3.69 (1H, d, B of ABq, J=18 Hz), 1.99 (1H, s); $^{13}$C NMR (CDCl$_3$) δ 170.1 (s), 159.7 (s), 156.3 (s), 138.7 (s), 138.6 (s), 134.0 (s), 128.4, 128.1, 127.3, 126.9, 125.7, 124.9 (s), 112.5 (d), 80.57 (d), 70.9 (d), 61.8 (t), 51.2 (t), 20.4 (q). Anal. C$_{24}$H$_{20}$NO$_7$SBr C, H, N.

EXAMPLE 17

Benzhydryl 7-[(Z)-t-butoxycarbonylmethylene] cephalosporanate (17)

To a solution of benzhydryl 7-oxocephalosporanate 2 (4.0 g, 9.2 mmol) in anhydrous CH$_2$Cl$_2$ (40 mL) at −78° C. was added a solution of ((tert-butoxycarbonyl)methylene) triphenylposphorane (3.45 g, 9.15 mmol in 40 mL CH$_2$Cl$_2$). The mixture was then stirred at −78° C. for 30 min. Acetic acid (1 mL) was added to quench the reaction and the reaction mixture was concentrated and purified by column chromatography to give title compound as a pale yellow solid. (yield=55%). R$_f$=0.52 in 2% EtOAc in CH$_2$Cl$_2$, mp 48°–50° C.; IR (CHCl$_3$) 3050, 1780, 1730 cm$^{-1}$; $^1$H NMR (CDCl$_3$) δ 7.36 (10H, m), 7.00 (1H, s), 6.39 (1H, s), 5.47 (1H, s), 5.00 (1H, d, A of ABq, J=13.48 Hz), 4.77 ( 1H, d, B of AB q, J=13.48 Hz), 3.62 (1H, d, A of ABq, J=18 Hz), 3.38 (1H, d, B of ABq, J=18 Hz), 2.02 (3H, s), 1.54 (9H, s); $^{13}$C NMR (CDCl$_3$) δ 170.2 (s), 162.4 (s), 160.5 (s), 157.8 (s), 150.1, (s), 139.0 (s), 138.8 (s), 128.3, 128.0, 127.9, 127.5, 126.9, 125.0 (s), 119.9 (d), 82.9 (s), 79.7 (d), 62.8 (t), 57.5 (d), 28.0 (q), 27.9 (t), 20.4 (q). Anal. (C$_{29}$H$_{29}$NO$_7$S) H, N, calc. C, 65.05; Found: C, 64.50.

EXAMPLE 18

Benzhydryl 7-[(Z)-(t-butoxycarbonyl)methylene]-cephalosporanate sulfone (18)

This compound was prepared from the corresponding sulfide 17 as described above for 5 to give a white solid (yield=73%). R$_f$=0.68 in 5% EtOAc in CH$_2$Cl$_2$; mp 58°–60° C. IR (CHCl$_3$) 3025, 1800, 1730, 1350, 1160 cm$^{-1}$; $^1$H NMR (CDCl$_3$) δ 7.36 (10H, m), 6.98 (1H, s), 6.59 (1H, s), 5.58 (1H, s), 5.14 (1H, d, A of ABq, J=14 Hz), 4.80 (1H, d, B of ABq, J=14 Hz), 4.12 (1H, d, A of ABq, J=18 Hz), 3.77 (1H, d, B of ABq, J=18 Hz), 2.04 (3H, s), 1.52 (9H, s); $^{13}$C NMR (CDCl$_3$) δ 170.0 (s), 161.5 (s), 159.4 (s), 157.1 (s), 142.3 (s), 138.6 (s), 138.5 (s), 128.8, 128.4, 128.3, 127.2, 127.0, 125.9 (s), 123.5 (d), 83.8 (s), 80.2 (d), 71.6 (d), 61.3 (t), 52.8 (t), 27.6 (q), 20.2 (q); high-resolution mass spectrum for [C$_{29}$H$_{29}$NO$_9$SNa]$^+$, i.e. [M+Na]$^+$, m/z calcd 590.1461, found 590.1447.

EXAMPLE 19

Benzhydryl 7-[(Z)-formylmethylene] cephalosporanate (19)

This compound was prepared from 2 and (triphenylphosphoranylidene)acetaldehyde using the procedure described for the preparation of compound 17 (yield= 46%). R$_f$=0.37 in 2% EtOAc in CH$_2$Cl$_2$; mp 113°–115° C.; IR (CHCl$_3$) 3050, 1780, 1730, 1700 cm$^{-1}$; $^1$H NMR (CDCl$_3$) δ 9.80 (1H, d, J=6.1) 7.34 (10H, m), 6.99 (1H, s), 6.60 (1H, d, J=6.1 Hz), 5.45 (1H, s), 5.00 (1H, d, A of ABq, J=13.51 Hz), 4.75 (1H, d, B of ABq, 13.55 Hz), 3.64 (1H, d, A of ABq, J=18.59 Hz), 3.41 (1H, d, B of ABq, J=18.61 Hz), 2.00 (3H, s); $^{13}$C NMR (CDCl$_3$) δ 188.2 (d), 170.1 (s), 160.3 (s), 157.0 (s), 154.7 (s), 138.9 (s), 138.8 (s), 128.4, 128.1, 128.0, 127.6, 126.9, 126.7, 125.0 (s), 123.5 (d), 79.9 (d), 62.4 (t), 56.4 (d), 28.1 (t), 20.4 (q); high-resolution mass spectrum for [C$_{25}$H$_{21}$NO$_6$SNa]$^+$, i.e. [M+Na]$^+$, m/z calcd 486.0987, found 468.0981. Minor product E-isomer; $^1$H NMR (CDCl$_3$) d 10.28 (1H, d, J=7.6) 7.34 (10H, m), 6.99 (1H, s), 6.26 (1H, d, J=7.6 Hz), 5.28 (1H, s), 5.00 (1H, d, A of ABq, J=13.5 Hz), 4.75 (1H, d, B of ABq, 13.5 Hz), 3.60 (1H, d, A of ABq, J=18.6 Hz), 3.40 (1H, d, B of ABq, J=18.6 Hz), 2.00 (3H, s).

EXAMPLE 20

Benzhydryl 7-[(Z)-(2'-pyridyl)methylene] cephalosporanate (20)

To a solution of 2-picolyl chloride hydrochloride (13.1 g, 80 mmol) in water (20 mL) was added K$_2$CO$_3$ (11.0 g, 80 mmol). After the carbonate was completely dissolved, the solution was extracted with ether (3×10 mL). The combined organic layers were washed with saturated NaCl solution (1×30 mL), dried (Na$_2$SO$_4$) and concentrated to give picolyl chloride (9.2 g, 90%). Picolyl chloride (8.9 g, 70 mmol), triphenylphosphine (18.3 g, 70 mmol) and 1,4-dioxane (30 mL) were mixed and refluxed for 24 h. The reaction mixture was washed with ether (2x30 mL) and the remaining solid was dried in vacuo to give a white solid (25.5 g, 94%). A mixture of 2-picolyltriphenylphosphonium chloride (5.8 g, 15 mmol) and sodium amide (0.58, 15 mmol) in THF (15 mL) was stirred at rt for 30 min. The resulting brown suspension was cooled to −78° C. and a solution of benzhydryl 7-oxocephalosporanate 2 (6.6 g, 15 mmol) in THF (15 mL) was added in one portion and the mixture was stirred at −78° C. for 15 min. The reaction was quenched by the addition of saturated ammonium chloride solution (10 mL) and the reaction mixture extracted with EtOAc (2×20 mL). The combined organic layers were washed with water (2×40 mL), dried over MgSO$_4$, concentrated and purified by column chromatography to obtain a yellow solid (2.9 g, 38%). R$_f$=0.28 in 2% EtOAc in CH$_2$Cl$_2$; mp 181°–183° C.; IR (CHCl$_3$) 3060, 1810, 1750 cm$^{-1}$; $^1$H NMR (CDCl$_3$) δ 8.68 (1H, d), 7.72 (1H, t), 7.35(12H, m), 7.15 (1H, s), 7.10 (1H, s), 5.66 (1H, s), 4.96 (1H, d, A of ABq, 13 Hz), 4.73 (1H, d, B of ABq, J=13 Hz), 3.63 (1H, d, A of ABq, J=18 Hz), 3.63 (1H, D, B of ABq, J=18 Hz), 2.01 (3H, s); $^{13}$C NMR (CDCl$_3$) δ 170.3 (s), 161.0 (s), 160.2 (s), 151.6 (d), 150.1 (s), 140.6 (s), 139.3 (s), 139.1 (s), 136.6 (d), 128.3, 127.9, 127.8, 127.6, 127.2, 126.9, 125.8 (s), 123.9 (s), 123.5 (s), 79.5 (d), 63.0 (t), 58.5 (d), 28.0 (t), 20.5 (q); high-resolution mass spectrum for [C$_{29}$H$_{24}$N$_2$O$_5$SNa]$^+$, i.e. [M+Na]$^+$, m/z calcd 535.1304, found 535.1300.

EXAMPLE 21

Benzhydryl 7-[(Z)-(2'-pyridyl)methylene] cephalosporanate sulfone (21)

This compound was prepared from the corresponding sulfide 21 (0.45 g, 0.88 mmol) as described for 5 to give a white solid (yield=90%). R$_f$=0.26 in 2% EtOAc in CH$_2$Cl$_2$; mp 120°–122° C.; IR (CHCl$_3$) 2975, 2950, 1780, 1720, 1340, 1130 cm$^{-1}$; $^1$H NMR (CDCl$_3$) δ 8.67 (1H, d), 7.71 (1H, t), 7.40 (13H, m), 7.00 (1H, s), 5.91 (1H, s), 5.14 (1H, d, A of ABq, J=14 Hz), 4.80 (1H, B of ABq, J=14 Hz), 4.11 (1H, d, A of ABq, J=18 Hz), 3.78 (1H, d, B of ABq, J=18 Hz), 2.05 (3H, s); high-resolution mass spectrum for [C$_{29}$H$_{24}$N$_2$O$_7$SNa]$^+$, i.e. [M+Na]$^+$, m/z calcd 567.1202, found 567.1198.

EXAMPLE 22

Benzhydryl 7-[dichloromethylene]cephalosporanate (22)

CCl$_4$ (2 mL, 20.7 mmol) was added into a solution of PPh$_3$ in anhydrous CH$_3$CN (50 mL) and stirred at rt for 30 min. This solution was transferred into a solution of benzhydryl 7-oxocephalosporanate 2 (3.0 g, 8.9 mmol) in anhydrous $CH_3CN$ (20 mL) and Zn/Cu (1.0 g, 15 mmol) was added. This reaction mixture was further stirred at rt for 40 min. The unreacted Zn/Cu was removed by filtration and the filtrate was concentrated and purified by column chromatography ($CH_2Cl_2$) to yield a pale yellow solid (2.70 g, 78%). $R_f$=0.73 in $CH_2Cl_2$; mp 48°–50° C.; IR ($CHCl_3$) 3050, 1780, 1740, 940 $cm^{-1}$; $^1H$ NMR ($CDCl_3$) δ 7.38 (10H, m), 6.99 (1H, s) 5.29 (1H, s), 5.02 (1H, d, A of ABq, J=13 Hz), 4.76 (1H, d, B of ABq, J=13 Hz), 3.57 (1H, d, A of ABq, J=18 Hz) 3.88 (1H, d, B of ABq, J=18 Hz), 2.04 (3H, s); $^{13}C$ NMR ($CDCl_3$) δ 170.0 (s), 160.2 (s), 154.5 (s), 138.8 (s), 138.7 (s), 136.2 (s), 128.1, 127.7, 127.2, 126.6, 126.2, 124.7 (s), 123.6 (s), 79.8 (d), 62.8 (t), 57.4 (d), 26.9 (t), 20.3 (q); high-resolution mass spectrum for $[C_{24}H_{19}NO_5SCl_2Na]^+$, i.e. $[M+Na]^+$, m/z calcd 526.0259, found 526.0251.

EXAMPLE 23

Benzhydryl 7-[dichloromethylene]cephalosporanate sulfone (23)

This compound was prepared from the corresponding sulfide 22 as described above for compound 5 to give a white solid (yield=81%). $R_f$=0.38 in 2% EtOAc in $CH_2Cl_2$; mp 64°–66° C.; IR ($CHCl_3$) 3050, 1800, 1740, 1350, 1140 $cm^{-1}$; $^1H$ NMR ($CDCl_3$) δ 7.35 (10H, m), 6.95 (1H, s), 5.28 (1H, s), 5.05 (1H, d, A of ABq, 14 Hz), 4.65 (1H, d, B of ABq, 14 Hz), 4.03 (1H, d, A of ABq, J=18 Hz), 3.80 (1H, B of ABq, 18 Hz), 2.04 (3H, s); $^{13}C$ NMR ($CDCl_3$) δ 170.2 (s), 159.6 (s), 153.9 (s), 138.6 (s), 138.5 (s), 134.3 (s), 130.2 (s), 128.9, 128.6, 128.3, 127.6, 127.3, 127.1, 124.3 (s), 80.7 (d), 70.7 (d), 61.9 (t), 51.7 (t), 20.5 (q). Anal. $C_{24}H_{19}NO_7SCl$: C, H, N.

EXAMPLE 24

Benzhydryl 7-[(Z)-methoxycarbonylmethylene]cephalosporanate (24)

This compound was prepared from 2 and methyl (triphenylphosphoranylidene)acetate using the procedure described for the preparation of compound 17 (a pale yellow solid, 68%). $R_f$=0.42 in 2% EtOAc in $CH_2Cl_2$; mp. 47°–49° C.; IR ($CHCl_3$) 3050, 1790, 1730, $cm^{-1}$; $^1H$ NMR ($CDCl_3$) δ 7.36 (10H, m), 7.00 (1H, s), 6.49 (1H, s), 5.50 (1H, s), 5.00 (1H, d, A of ABq, J=13.5 Hz), 4.76 (1H, d, B of ABq, J=13.5 Hz), 3.84 (3H, s), 3.64 (1H, d, A of ABq, J=18.8 Hz), 3.39 (1H, d, B of ABq, J=18.8 Hz), 2.03 (3H, s); $^{13}C$ NMR ($CDCl_3$) δ 170.3, 163.8, 160.6, 157.5, 152.6, 139.2, 139.0, 128.6, 128.3, 127.9, 127.6, 127.3, 126.9, 125.5, 117.5, 79.9, 62.9, 57.9, 52.5, 27.9, 20.6. Anal. Calcd for $C_{26}H_{23}NO_7S$: C, 63.29; H, 4.66; N, 2.84. Found: C, 63.47; H, 4.73; N, 2.87.

EXAMPLE 25

Benzhydryl 7-[(Z)-(methoxycarbonyl)methylene]cephalosporanate sulfone (25)

This compound was prepared from the corresponding sulfide 24 as described above for compound 5 (white solid, 84%). $^1H$ NMR ($CDCl_3$) δ 7.34 (10H, m), 6.95 (1H, s), 6.65 (1H, s), 5.51 (1H, s), 5.09 (1H, d, A of ABq, J=14 Hz), 4.75 (1H, d, B of ABq, J=14 Hz), 4.05 (1H, d, A of ABq, J=10 Hz), 3.82 (3H, s), 3.79 (1H, B of ABq, J=10 Hz), 2.02 (3H, s); $^{13}C$ NMR ($CDCl_3$) δ 170.3 (s), 163.7 (s), 160.6 (s), 157.6 (s), 152.5(s), 139.3 (s), 139.2 (s), 128.7, 128.5, 128.2, 128.1, 127.7, 127.0(s), 126.6, 125.7, 117.6 (d), 79.8 (s), 78.2 (d), 62.9 (t), 57.8 (d),52.5, 27.9 (q), 20.6 (q). Anal. Calcd for $C_{26}H_{23}NO_9S$: C, 59.42 ; H, 4.41; N, 2.66 Found: C, 59.16; H, 4.30, N, 2.86.

EXAMPLE 26

Benzhydryl 7-[(Z)-(hydroxymethyl)methylene] cephalosporanate (26)

To a solution of 19 (0.75 g, 1.62 mmol) in methanol (10 mL) and acetic acid (1 mL) was added $NaCNBH_3$ (0.51 g, 8.1 mmol) in one portion, and stirred at rt for 30 min. The reaction mixture was concentrated in vacuo, and the residue was dissolved in EtOAc (25 mL) and water (10 mL). The aqueous layer was exacted with EtOAc (1×30 mL), and the combined organic layer was washed with water (1×30 mL), dried ($Na_2SO_4$), concentrated and purified by column chromatography to give a white solid (0.71 g, 94%). $R_f$=0.3 in 10% EtOAc in $CH_2Cl_2$; mp 58°–60° C.; $^1H$ NMR ($CDCl_3$) δ 7.39 (10H, s), 7.01 (1H, s), 6.51 (1H, s), 5.29 (1H, s), 4.94 (1H, d, A of ABq, J=13 Hz), 4.71 (1H, d, B of ABq, J=13 Hz), 4.60 (1H, d, A of ABq, J=20.83 Hz), 4.42 (1H, d, B of ABq, J=20.22 Hz), 3.56 (1H, d, A of ABq, J=18 Hz), 3.33 (1H, d, B of ABq, J=18 Hz), 2.01 (3H, s); $^{13}C$ NMR ($CDCl_3$) δ 170.5 (s), 161.2 (s), 159.9 (s), 139.0 (s), 138.8 (s), 137.4 (s), 131.8 (d), 128.3, 128.0, 127.9, 127.6, 127.4, 126.8, 122.2 (s), 79.6 (d), 63.0 (t), 60.0 (t), 56.9 (d), 28.0 (t), 20.5 (q); high-resolution mass spectrum for $[C_{25}H_{23}NO_6SNa]^+$, i.e. $[M+Na]^+$, m/z calcd 488.1144, found 488.1138.

EXAMPLE 27

Benzhydryl 7-[(Z)-N-methoxy-N-methylaminocarbonylmethylene]cephalosporanate sulfone (27)

To a solution of benzhydryl 7-oxocephalosporanate 2 (1.0 g, 2.3 mmol) in anhydrous $CH_2Cl_2$ (20 mL) at –78° C. was added N-methoxy-N-methyl-2-(triphenylphosphoranylidene)acetamide (0.73 g, 2.0 mmol). The mixture was stirred at –78° C. for 10 min, and then warmed to 0° C. and further stirred for 15 min. Acetic acid (0.5 mL) was added to quench the reaction, and the reaction mixture was concentrated and purified by column chromatography (2% EtOAc in $CH_2Cl_2$) to give benzhydryl 7-[(Z)-N-methoxy-N-methylaminocarbonylmethylene cephalosporanate as a pale yellow solid (0.53 g, 51%). IR ($CHCl_3$) 3050, 1780, 1730 $cm^{-1}$; $^1H$ NMR ($CDCl_3$) δ 7.35 (10H, m), 7.06 (1H, s), 7.00 (1H, s), 5.56 (1H, s), 4.96 (1H, d, A of ABq, J=13 Hz), 4.75 (1H, d, B of ABq, J=13 Hz), 3.75 (3H, s), 3.64 (1H, d, B of ABq, J=19 Hz), 3.37 (1H, d, B of ABq, J=19 Hz), 3.28 (3H, s), 2.01 (3H, s); $^{13}C$ NMR ($CDCl_3$) δ 170.4 (s), 163.1 (s), 160.8 (s), 158.5 (s), 151.2 (s), 139.2 (s), 139.0 (s), 128.5, 128.4, 128.1, 128.0, 127.8, 127.0, 124.8 (s), 115.6 (d), 79.8 (d), 63.0 (t), 62.4 (q), 58.0 (d), 32.2 (q), 28.1 (t), 20.6 (q).

This compound was oxidized to the corresponding sulfone as described above for 5 to give a white solid (yield= 68%). $R_f$=0.44 in 25% EtOAc in $CH_2Cl_2$; mp 81°–82° C.; IR ($CHCl_3$) 3050, 1800, 1740, 1360, 1140 $cm^{-1}$; $^1H$ NMR ($CDCl_3$) δ 7.36 (10H, m), 7.28 (1H, s), 6.98 (1H, s), 5.72 (1H, s), 5.10 (1H, d, A of ABq, J=14 Hz), 4.82 (1H, d, B of ABq, J=14 Hz), 4.11 (1H, d, A of ABq, J=17 Hz), 3.78 (1H, d, B of ABq, J=17 Hz), 3.78 (3H, s), 3.31 (3H, s), 2.06 (3H, s); $^{13}C$ NMR ($CDCl_3$) δ 170.1 (s), 162.1 (s), 159.7 (s), 157.8 (s), 142.78 (s), 138.9 (s), 138.8 (s), 128.7, 128.4, 127.7, 127.4, 127.1, 126.9, 125.7 (s),., 119.3 (d), 80.3 (d), 72.3 (d), 62.5 (q), 61.8 (t), 52.9 (t), 32.3 (q), 20.5 (q); high-resolution mass spectrum for $[C_{27}H_{26}N_2O_9SNa]^+$, i.e. $[M+Na]^+$, m/z calcd 577.1257, found 577.1247.

EXAMPLE 28

Benzhydryl 7-[(Z)-acetylmethylene] cephalosporanate (28)

This compound was prepared from 2 and triphenylphosphoranylidene-2-propanone using the procedure described for the preparation of compound 17 (yield=58%). $R_f$=0.29 in 2% EtOAC in $CH_2Cl_2$; mp 49°–50° C.; IR ($CHCl_3$) 3000, 1770, 1720 $cm^{-1}$; $^1H$ NMR ($CDCl_3$) δ 7.36 (10H, m), 7.00 (1H, s), 6.48 (1H, s), 5.50 (1H, s), 5.00 (1H, d, A of ABq, J=13 Hz), 4.77 (1H, d, B of ABq, J=13 Hz), 3.63 (1H, d, A of ABq, J=19 Hz), 3.38 (1H, d, B of ABq, J=19 Hz), 2.39 (3H, s), 2.02 (3H, s). $^{13}C$ NMR ($CDCl_3$) δ 195.8 (s), 170.3 (s), 160.6 (s), 158.5 (s), 149.5 (s), 139.3 (s), 139.1 (s), 128.5, 127.8, 127.1, 126.9, 126.3, 125.6 (s), 122.7 (d), 79.8 (d), 63.0 (t), 58.0 (d), 30.9 (q), 28.0 (t), 20.7 (q). Anal. ($C_{26}H_{23}NO_6S$) C, H, N.

EXAMPLE 29

Benzhydryl 7-[(Z)-acetylmethylene] cephalosporanate sulfone (29)

This compound was prepared from the corresponding sulfide 28 as described for 5 to give a white solid (yield=79%). $R_f$=0.66 in 25% EtOAc in $CH_2Cl_2$; mp 176°–178° C.; IR ($CHCl_3$) 3050, 1800, 1730, 1350, 1140 $cm^{-1}$; $^1H$ NMR ($CDCl_3$) δ 7.38 (10H, m), 6.99 (1H, s), 6.94 (1H, s), 5.64 (1H, s), 5.13 (1H, d, A of ABq, J=14 Hz), 4.81 (1H, d, B of ABq, J=14 Hz), 4.12 (1H, d, A of ABq, J=18 Hz), 3.80 (1H, d, B of ABq, J=18 Hz), 2.46 (3H, s), 2.07 (3H, s). $^{13}C$ NMR ($CDCl_3$) δ 194.7 (s), 170.1 (s), 159.5 (s), 157.5 (s), 141.2 (s), 138.7 (s), 138.6 (s), 128.6, 128.3, 127.5, 127.1, 126.8 (s), 125.3 (d), 80.5 (d), 72.2 (d), 61.7 (t), 53.1 (t), 31.0 (q), 20.5 (q); high-resolution mass spectrum for $[C_{26}H_{23}NO_8SNa]^+$, i.e. $[M+Na]^+$, m/z calcd 532.1042, found 532.1045.

EXAMPLE 30

Benzhydryl 7-[(Z)-cyanomethylene] cephalosporanate (30)

This compound was prepared from (cyanomethylene) triphenylphosphorane and 2 using a minor modification of the procedure described above for the preparation of 17 (the reaction was warmed to room temperature and stirred for an additional hour, while monitoring by tlc). (Yield=52%). $^1H$ NMR ($CDCl_3$) δ 7.6–7.3 (10 H, m), 7.03 (1H, s), 6.12 (1H, s), 5.43 (1H, s), 5.08, 5.05 (1H, d, J=14 Hz), 4.85, 4.82 (1H, d, J=14 Hz), 3.67, 3.62 (1H, d, J=18.5 Hz),3.49, 3.44 (1H, d, J=18.5 Hz), 2.06 (3H, s). $^{13}C$ NMR ($CDCl_3$) δ 170.4, 160.3, 158.3, 139.0, 128.9, 127.1, 113.1, 97.9, 80.2, 63.0, 56.9, 27.8, 20.7.

EXAMPLE 31

Benzhydryl 7-[(Z)-cyanomethylene] cephalosporanate sulfone (31)

This compound was prepared from the corresponding sulfide 30 using a procedure analogous to that described for 5 above. (Yield=55%). $^1H$ NMR ($CDCl_3$) δ 7.6–7.2 (10 H, m), 6.89 (1H, s), 6.24 (1H, s), 5.29 (1H, s), 5.04, 5.01 (1H, d, J=14.5 Hz), 4.70, 4.67 (1H, d, J=14.5 Hz), 4.04, 3.99 (1H, d, J=18.5 Hz), 3.79, 3.74 (1H, d, J=18.5 Hz), 1.96 (3H, s). $^{13}C$ NMR ($CDCl_3$) δ 170.2, 159.2, 154.4, 149.7, 138.6, 138.5, 128.7, 127.7, 127.2, 112.3, 101.9, 80.9, 70.0, 61.9, 52.3, 20.6.

EXAMPLE 32

Benzhydryl 7-{[(E)-bromo-(Z)-methoxycarbonyl] methylidene} cephalosporanate (32)

This compound was prepared from 2 and methyl bromo-(triphenylphosphoranylidene)acetate using the procedure described for the preparation of compound 17 (yield=68%). $^1H$ NMR ($CDCl_3$) δ 7.6–7.2 (10 H, m), 6.85 (1H, s), 5.48 (1H, s), 4.98 4.95 (1H, d, J=14 Hz), 4.76, 4.73 (1H, d, J=14 Hz), 3.81 (3H, s), 3.57, 3.52 (1H, d, J=18.5 Hz), 3.37, 3.32 (1H, d, J=14 Hz), 2.02 (3H, s).

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of treating an elastase-mediated pathology, comprising the administration to a mammal in need of such treatment an effective amount of a compound of formula I:

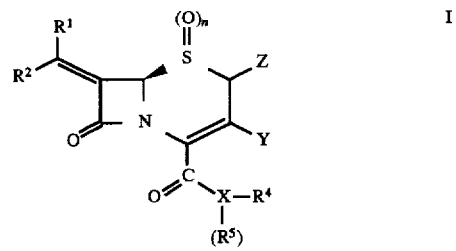

wherein n=0, 1, or 2;

$R^1$ and $R^2$ are the same or different and are:
- a) hydrogen;
- b) halo;
- c) ($C_1$–$C_{10}$)alkoxycarbonyl;
- d) cyano;
- e) ($C_1$–$C_{10}$)alkoxycarbamido;
- f) a 5-7 membered heterocyclic ring;
- g) ($C_1$–$C_{10}$)alkyl;
- h) ($C_2$–$C_{10}$)acyl;
- i) ($C_1$–$C_{10}$)alkoxy;
- j) ($C_2$–$C_{10}$)alkanoyloxy;
- k) $N(R)_2$, wherein R is H, ($C_1$–$C_{10}$)alkyl, phenyl or benyl;
- l) $(R)_2NC(O)$—;
- m) $NO_2$;
- n) N=O;
- o) S(R);
- p) ($C_6$–$C_{10}$)aryl; or
- q) $CO_2H$;

Z is:
- a) halo;
- b) CHO;
- c) $CO_2H$;
- d) CN;
- e) ($C_1$–$C_{10}$)alkyl;
- f) ($C_6$–$C_{10}$)aryl;
- g) $C(O)R^7$;
- h) $CO_2R^7$;
- i) $OR^7$;
- j) $OC(O)R^7$;
- k) $SR^7$;
- l) $SC(O)R^7$;
- m) $N(R^7)_2$; or
- n) H;

Y is:
a) —$CH_2A$ wherein A is
   (i) H;
   (ii) halo;
   (iii) OH;
   (iv) ($C_1$–$C_{10}$)alkoxy;
   (v) ($C_6$–$C_{10}$)aryloxy;
   (vi) ($C_2$–$C_{10}$)acyloxy;
   (vii) —$N(R)C(O)R^7$
   (viii) —$N(R)_2$;
   (ix) S(R); or
   (x) $SC(O)(C_1$–$C_{10})$alkyl;
b) halo;
c) CHO;
d) $CO_2H$;
e) CN;
f) ($C_1$–$C_{10}$)alkyl;
g) ($C_6$–$C_{10}$)aryl;
h) $C(O)R^7$;
i) $CO_2R^7$;
j) $OR^7$;
k) $OC(O)R^7$;
l) $SR^7$;
m) $SC(O)R^7$; or
n) $N(R^7)_2$; wherein each $R^7$ is ($C_1$–$C_{10}$)alkyl, ($C_6$–$C_{10}$) aryl, or a 5-10 membered heterocyclic ring;

X is $CR^8$, O, S or N;

$R^4$ and $R^5$, if present, are the same or different and are:
a) ($C_1$–$C_{10}$)alkyl;
b) ($C_6$–$C_{10}$)aryl; preferably phenyl;
c) a 5-10 membered heterocyclic ring; or
d) H; with the proviso that if X is O, $R^4$ is not H; wherein $R^8$ is H or $R^4$; wherein alkyl or alkoxy are optionally substituted with 1-3 ($C_1$–$C_{10}$)alkyl, OH, halo, phenyl or mixtures thereof; wherein aryl or aryloxy are optionally substituted with 1-3 ($C_1$–$C_4$)alkyl, OH, ($C_1$–$C_4$)alkoxy, halo, phenyl or mixtures thereof; wherein the heterocyclic ring comprises 1-3 $N(R^9)$, S or nonperoxide O, wherein $R^9$ is absent or is H, ($C_1$–$C_4$)alkyl, phenyl or benzyl; or a pharmaceutically acceptable salt thereof.

2. The method of claim 1 wherein n is 1 or 2.
3. The method of claim 1 wherein n is 2.
4. The method of claim 1 or 2 wherein Z is H.
5. The method of claim 1 or 2 wherein X is CH.
6. The method of claim 5 wherein $R^4$ and $R^5$ are ($C_6$–$C_{10}$) aryl.
7. The method of claim 6 wherein $R^4$ and $R^5$ are phenyl.
8. The method of claims 1, 2 or 4 wherein $R^2$ is H.
9. The method of claim 8 wherein $R^1$ is ($C_6$–$C_{10}$)aryl.
10. The method of claim 9 wherein $R^1$ is phenyl.
11. The method of claim 8 wherein $R^1$ is ($C_1$–$C_{10}$) alkoxycarbonyl.
12. The method of claim 8 wherein $R^1$ is CHO.
13. The method of claim 8 wherein $R^1$ is a 5-7 membered heterocyclic ring.
14. The method of claim 8 wherein $R^1$ is ($C_2$–$C_{10}$)acyl.
15. The method of claim 14 wherein $R^1$ is acetyl.
16. The method of claim 8 wherein $R^1$ is CN.
17. The method of claim 8 wherein $R^1$ is halo.
18. The method of claim 8 wherein $R^1$ is ($C_1$–$C_{10}$)alkoxy.
19. The method of claim 8 wherein $R^1$ and $R^2$ are halo.
20. The method of claims 1, 2 or 4 wherein $R^2$ is ($C_6$–$C_{10}$)aryl.
21. The method of claims 1, 2 or 4 wherein $R^2$ is halo.
22. The method of claim 21 wherein $R^2$ is Br.
23. The method of claim 22 wherein $R^1$ is ($C_1$–$C_{10}$) alkoxycarbonyl.
24. The method of claims 1, 2 or 4, wherein Y is ($C_2$–$C_{10}$)acyloxymethyl.
25. The method of claim 1 wherein the mammal is a human.
26. A method of treating an elastase-mediated pathology, comprising administering to a mammal in need of such treatment an effective amount of a compound of formula:

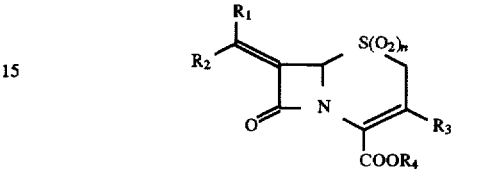

wherein n is 0 or 1;
$R_1$ and $R_2$ are the same or different and are:
a) hydrogen;
b) $C_{1-10}$-alkyl;
c) halogen;
d) hydroxy-$C_{1-10}$-alkyl;
e) $C_{1-10}$-alkoxy;
f) $C_{2-10}$-alkanoyloxy;
g) $C_{1-10}$-alkoxycarbonyl;
h) N—$C_{1-10}$-alkoxy-N—$C_{1-10}$-alkylaminocarbonyl;
i) $C_{6-10}$-aryl;
j) a 5-10 membered heterocyclic ring having from 1-3 heteroatoms selected from the group consisting of nonperoxide O, N(R) and S; wherein R is absent or is H, ($C_1$–$C_4$)alkyl, phenyl or benzyl; or
k) —COOH or —COOY, wherein Y is pharmaceutically acceptable cation;

$R_3$ is —$CH_2M$ where M is selected from the group consisting of
a) hydrogen;
b) halogen;
c) hydroxy;
d) $C_{1-10}$-alkoxy;
e) $C_{6-10}$-aryloxy;
f) $C_{6-10}$-aryl-$C_{1-10}$-alkoxy;
g) mercapto, optionally substituted with one or more groups selected from the group consisting of methyl, ethyl or phenyl;
h) $C_{2-10}$-acylthio;
i) $C_{2-10}$-acyloxy or $C_{2-10}$-carbamoyloxy; or
j) amino, optionally substituted with one or two $C_{1-10}$-alkyl groups;

$R_4$ is $C(R^5)(R^6)(R^7)$, wherein $R^5$, $R^6$ and $R^7$ are individually H, ($C_1$–$C_{10}$)alkyl, ($C_6$–$C_{10}$)aryl or a 5-7 membered heterocyclic ring, comprising 1-3 N(R), S or nonperoxide O; wherein R is absent or is H, ($C_1$–$C_4$)alkyl, phenyl or benzyl; or a pharmaceutically acceptable salt thereof.

27. The method of claim 26 wherein M is acetoxy.
28. The method of claim 27 wherein $R^5$ is H and $R^6$ and $R^7$ are ($C_6$–$C_{10}$)aryl.
29. The method of claims 27 or 28 wherein n is O, $R_2$ is hydrogen and $R_1$ is selected from the group consisting of t-butyl, phenyl, ($C_1$–$C_4$)alkoxycarbonyl, pyridyl, acetyl, and CN.

30. The method of claims 27 or 28 wherein n is 1, $R_2$ is hydrogen, and $R_1$ is $CO_2Me$, phenyl, $CO_2$-t-butyl, CHO, $CH_2OH$ and CN.

31. The method of claims 27 or 28 wherein n is 0 and $R_1$ and $R_2$ are both halo.

32. The method of claims 27 or 28 wherein n is 1 and $R_1$ and $R_2$ are the same and are bromo or chloro.

33. The method of claims 27 or 28 wherein n is 1, $R_1$ is —$CO_2(C_1$–$C_4)$alkyl, and $R_2$ is bromo.

34. The method of claims 27 or 28 wherein n is 1, $R_1$ is hydrogen and $R_2$ is $(C_6$–$C_{10})$aryl.

35. The method of claims 27 or 28 wherein $R_3$ is $(C_1$–$C_4)$ alkanoyloxymethyl.

36. The method of claim 26 wherein the mammal is a human.

37. A compound of formula

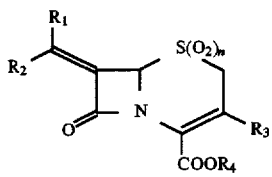

wherein n is 0 or 1;

$R_1$ and $R_2$ are the same or different and are:

a) H;

b) $(C_1$–$C_{10})$alkoxy;

c) cyano;

d) $(C_2$–$C_{10})$alkanoyloxy;

e) $(C_2$–$C_{10})$alkoxycarbamido; or f) $CO_2H$;

$R_3$ is $(C_2$–$C_{10})$alkanoyloxy; and $R_4$ is $C(R^5)(R^6)(R^7)$; wherein $R^5$, $R^6$ and $R^7$ are individually H, $(C_1$–$C_{10})$alkyl, $(C_6$–$C_{10})$aryl or a 5-10 membered heterocyclic ring comprising 1-3, N(R), S or nonperoxide O, wherein R is absent or is H, $(C_1$–$C_4)$ alkyl, phenyl or benzyl; or a pharmaceutically acceptable salt thereof.

38. A compound of claim 37 wherein $R_3$ is acetoxymethyl.

39. A compound of claim 37 wherein $R^5$ is H.

40. A compound of claim 37 wherein $R^6$ and $R^7$ are $(C_6$–$C_{10})$aryl.

41. A pharmaceutical composition comprising an amount of a compound of claim 37 capable of inhibiting a mammalian elastase in combination with a pharmaceutically acceptable carrier.

* * * * *